(12) United States Patent
Gypser et al.

(10) Patent No.: US 7,449,471 B2
(45) Date of Patent: Nov. 11, 2008

(54) 5-PHENYLPYRIMIDINES, THEIR PREPARATION, COMPOSITIONS COMPRISING THEM AND THEIR USE

(75) Inventors: Andreas Gypser, Mannheim (DE); Thomas Grote, Wachenheim (DE); Anja Schwögler, Mannheim (DE); Joachim Rheinheimer, Ludwigshafen (DE); Frank Schieweck, Heβheim (DE); Jordi Tormo i Blasco, Limburgerhof (DE); Ingo Rose, Mannheim (DE); Peter Schäfer, Ottersheim (DE); Markus Gewehr, Kastellaun (DE); Wassilios Grammenos, Ludwigshafen (DE); Bernd Müller, Frankenthal (DE); Eberhard Ammermann, Heppenheim (DE); Siegfried Strathmann, Limburgerhof (DE); Gisela Lorenz, Hambach (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/677,862

(22) Filed: Feb. 22, 2007

(65) Prior Publication Data
US 2007/0149551 A1 Jun. 28, 2007

Related U.S. Application Data

(62) Division of application No. 10/495,280, filed as application No. PCT/EP02/12807 on Nov. 15, 2002.

(30) Foreign Application Priority Data
Nov. 19, 2001 (DE) ............................... 101 56 279

(51) Int. Cl.
C07D 239/42 (2006.01)
C07D 239/30 (2006.01)
A61K 31/505 (2006.01)
A61K 31/506 (2006.01)
A01N 43/54 (2006.01)

(52) U.S. Cl. .................. 514/256; 514/269; 514/272; 514/275; 544/326; 544/334; 544/317; 544/320; 544/325

(58) Field of Classification Search .............. 544/317, 544/320, 325, 326, 334; 514/272, 275, 256
See application file for complete search history.

(56) References Cited

U.S. PATENT DOCUMENTS

| | | | | |
|---|---|---|---|---|
| 3,919,229 | A * | 11/1975 | Carraz et al. ............... | 544/325 |
| 5,142,060 | A | 8/1992 | Müller et al. ............. | 548/263.8 |
| 5,250,530 | A | 10/1993 | Glencke et al. ............ | 514/256 |
| 5,591,746 | A | 1/1997 | Miller et al. ............... | 514/255 |
| 5,597,827 | A | 1/1997 | Miller et al. ............... | 514/255 |
| 7,153,860 | B2 | 12/2006 | Grote et al. ................ | 514/256 |

FOREIGN PATENT DOCUMENTS

| | | |
|---|---|---|
| DE | 42 27 811 | 2/1994 |
| EP | 0251 083 | 1/1988 |
| EP | 0 407 899 | 1/1991 |
| EP | 0 727 214 | 8/1996 |
| GB | 2 277 090 | 10/1994 |
| WO | WO 92/10490 | 6/1992 |
| WO | WO 99/19305 | 4/1999 |
| WO | WO 01/96314 | 12/2001 |
| WO | WO 02/074753 | 9/2002 |

OTHER PUBLICATIONS

Griffin et al., J. Chem. Soc. Perkin I., 14, 1811-1819, 1992.*
Chen et al., Yaoxue Xuebao, 17(9), 674-81, 1982; CA 98: 53154, 1983.*

(Continued)

Primary Examiner—Venkataraman Balasubram
(74) Attorney, Agent, or Firm—Novak Druce + Quigg LLP

(57) ABSTRACT

5-Phenylpyrimidines of the formula I

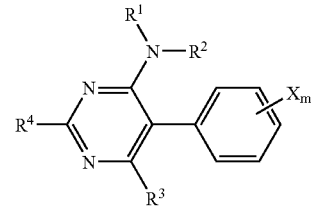

in which the substituents and the index are as defined below:
$R^1, R^2$ are hydrogen, alkyl, haloalkyl, cycloalkyl, halocycloalkyl, alkenyl, haloalkenyl, alkynyl or haloalkynyl, and $R^1$ and $R^2$ together with the nitrogen atom to which they are attached may also form a saturated or unsaturated ring which may be interrupted by an ether, thio, sulfoxyl or sulfonyl group and may be substituted by one to four groups $R^a$ and/or $R^b$;
$R^3$ is hydrogen, halogen, cyano, alkyl, haloalkyl, alkoxy, haloalkoxy or alkenyloxy;
$R^4$ is hydrogen, halogen, cyano, hydroxyl, mercapto, azido, alkyl, alkenyl, alkynyl, haloalkyl, alkoxy, alkenyloxy, alkynyloxy, haloalkoxy, alkylthio, alkenylthio, alkynylthio, haloalkylthio, —ON═$CR^aR^b$, —$CR^c$═$NOR^a$, —$NR^cN$═$CR^aR^b$, —$NR^aR^b$, —$NR^cNR^aR^b$, —$NOR^a$, —$NR^cC$(═$NR^a$)$NR^aR^b$, —$NR^cC$(═O)$NR^aR^b$, —$NR^aC$(═O)$R^c$, —$NR^aC$(═$NOR^c$)$R^a$, —OC(═O)$R^c$, —C(═$NOR^c$)$NR^aR^b$, —$CR^c$(═$NNR^aR^b$), —C (═O) $NR^aR^b$ or —C(═O)$R^c$;
in which $R^a$, $R^b$ and $R^c$ are as defined in the description;
X is halogen, alkyl, alkoxy or haloalkyl; and
m is an integer from 1 to 5 ;
processes for preparing these compounds, compositions comprising them and their use for controlling harmful fungi are described.

2 Claims, No Drawings

OTHER PUBLICATIONS

Silveira et al., Revista de Farmacia e Bioquimica da Universidade de Sao Paulo, 17(1), 47-59, 1981; CA 96: 149095, 1982.*

Zielinski et al., Heterocycles 36(7), 1521-1528 (1993); "A simple method for synthesis of 4-di-methylamino-2,6-dimethyl-5-phenylpyrimidines".

Zielinski et al., Chemical Abstracts vol. 125(17), 221864m (1996) (XP002230224); "Preparation of 4-aminopyrimidines and 4-aminoquinazolines".

Masuda et al., Chemical Abstracts vol. 114(5), 57530z (1991) (XP002230225); "2-iodopropar-gyloxypyrimidines and agrochemical microbicides containing them".

Newkome et al., J. Org. Chem. 31, 677-681 (1966); "Synthesis of simple Hadrazones of Carbonyl Compounds by an Exchange Reaction".

Park et al., Bull. Korean Chem. Soc. 16(6), 489-492 (1995); "A New Synthesis of a Chiral Ester Containing Phenylpyrimidine Ring as Liquid Crystal Dopant".

Tumkevlcius, Liebigs Ann. Chem. 1995, 1703-1705; "A Facile Synthesis of 5H-1-Thia-3,5,6,8-tetraazaacenaphthylenes".

Reddy et al., Heteroatom Chem. 10(1), 17-23 (1999); "5,7-Diarylspiro[4,5,6,7-tetrahydro-benzo[d][1,2,3]selena/thiadiazole-6,5'-(hexahydropyrimidine)]-2',4',6',-triones/2'-thioxo-4',6',-diones from Cyclohexanonedicarboxylates".

Mangalagiu et al., Tetrahedron Lett. 37(8), 1309-1312 (1996); "Trialkylalanes in Palladium-Catalyzed Chemo- and Regioselective Alkylations".

Guillier et al., Chem. Eur. J. 5(12), 3450-3458 (1999); "Solid Phase Synthesis of 2,4,6-Triamino-pyrimidines".

Bátori et al., J. Heterocycl. Chem. 31(4), 1041-1046 (1994); "Synthesis of new v-Triazolopyrimidine Salts".

Baddiley et al., J. Chem. Soc. 1943, 383-386; "Experiments on the Synthesis of Purine Nucleosides. Part I".

Gundersen, Tetrahedron Lett. 35(19), 3155-3158 (1994); "6-Chloropurines and Organostannates in Palladium Catalyzed Cross Coupling Reactions".

Kenner et al., J. Chem. Soc. 1943, 388-390; "Some Reactions of Amidines with Derivatives of Malonic Acid".

Burdeska et al., Helv. Chim. Acta 64(11), 113-152 (1981); "Über die Herstellung von Styryl- und Stilbenyl-Derivatien des Pyrimidines" (About the preparation of styryl- and stilbenyl derivatives of pyrimidines).

Backer et al., Recl. Trav. Chim. Pays-Bas 61, 291-298 (1942); "Quelques Sulfanilamido-4-methylpyrimidines" (Some sulfanilamido-4-methylpyrimidines).

Sasaki et al., J. Heterocycl. Chem. 30(4), 993-995 (1993); "Polycyclic N-Heterocyclic Compounds. XLV."

Tumkevicius et al., J. Chem. Res. (S), 1995, 286-287; "Synthesis of 5-Alkyl-5H-1-thia-3,4,5,6,8-pentaazaacenaphthylenes".

Sakamoto et al., Chem. Pharm. Bull. 28(2), 571-577 (1980); "Studies on Pyrimidine Derivatives. XVI."

Honma et al., Chem. Pharm. Bull. 30(12), 4314-4324 (1982); "Studies on Antiallergic Agents. I."

Zaschke, Z. Chem. 17(2), 63-64 (1977); "Kristallin-flüssige 2-Cyanpyrimidine" (Crystallin-liquid 2-cyanopyrimidines).

Ahmed, Collect. Czech. Chem. Commun. 58, 2215-2221 (1993); "Novel Synthesis of 3-Spiroheterocycles-2-methylquinolin-4-one".

Kotva et al., Collect. Czech. Chem. Commun. 48, 137-143 (1983); "5,5-Disubstituted Barbituric Acids and their Analogues".

Havelková et al., Synlett 7, 1145-1147 (1999); "The Suzuki-Miyaura Cross-Coupling Reactions of 6-Holopurines with Boronic Acids Leading to 6-Aryl and 6-Alkenylpurines".

Henze et al., J. Org. Chem. 17, 1320-1327 (1952); "Researches on Pyrimidines: Certain Derivatives of 2-Methylpyrimidine".

Eicken et al., "4-Amino-pyrimidine derivatives"; esp@cenet English language Abstract of document AA.

* cited by examiner

5-PHENYLPYRIMIDINES, THEIR PREPARATION, COMPOSITIONS COMPRISING THEM AND THEIR USE

CROSS-REFERENCE TO RELATED APPLICATION(S)

This is a Divisional application of application Ser. No. 10/495,280, filed on May 11, 2004 (pending), the entire disclosure of which is herewith incorporated by reference, under 35 U.S.C. §371 as a national stage of International Application No. PCT/EP 02/12807, filed Nov. 15, 2002, the entire disclosure of which is herewith incorporated by reference.

The present invention relates to 5-phenylpyrimidine of the formula I

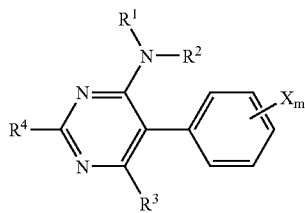

I where the substituents and the index are as defined below:

$R^1, R^2$ independently of one another are hydrogen, $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-haloalkenyl, $C_2$-$C_6$-alkynyl or $C_2$-$C_6$-haloalkynyl, $R^1$ and $R^2$ together with the nitrogen atom to which they are attached may also form a saturated or unsaturated five- or six-membered ring which may be interrupted by an ether-(—O—), thio-(—S—), sulfoxyl-(—S[=O]—)or sulfonyl-(—SO$_2$—)group and/or may be substituted by one to four groups $R^a$ and/or $R^b$;

$R^a, R^b$ independently of one another are hydrogen, $C_1$-$C_6$-alkyl, $C_2$-$C_8$-alkenyl, $C_2$-$C_8$-alkynyl, $C_1$-$C_6$-haloalkyl, $C_1$-$C_6$-alkoxy, $C_1$-$C_6$-haloalkoxy, $C_3$-$C_{10}$-cycloalkyl, phenyl or a five- to ten-membered saturated, partially unsaturated or aromatic heterocycle containing one to four heteroatoms from the group consisting of O, N and S, where the cyclic radicals may be partially or fully substituted by the following groups $R^x$:

$R^x$ independently of one another are cyano, nitro, amino, aminocarbonyl, aminothiocarbonyl, halogen, hydroxyl, $C_1$-$C_6$-alkyl, $C_1$-$C_6$-haloalkyl, $C_1$-$C_6$-alkyl-carbonyl, $C_1$-$C_6$-alkylsulfonyl, $C_1$-$C_6$-alkylsulfoxyl, $C_3$-$C_6$-cycloalkyl, $C_1$-$C_6$-alkoxy, $C_1$-$C_6$-haloalkoxy, $C_1$-$C_6$-alkyloxycarbonyl, $C_1$-$C_6$-alkylthio, $C_1$-$C_6$-alkylamino, di-$C_1$-$C_6$-alkylamino, $C_1$-$C_6$-alkyl-aminocarbonyl, di-$C_1$-$C_6$-alkylaminocarbonyl, $C_1$-$C_6$-alkylaminothiocarbonyl, di-$C_1$-$C_6$-alkylamino-thiocarbonyl, $C_2$-$C_6$-alkenyl, $C_2$-$C_6$-alkenyloxy, phenyl, phenoxy, benzyl, benzyloxy, 5- or 6-membered heterocyclyl, 5- or 6-membered hetaryl, 5- or 6-membered hetaryloxy, C(=NOR$^\alpha$)—OR$^\beta$or OC(R$^\alpha$)$_2$—C(R$^\beta$)=NOR$^\beta$, where the cyclic groups for their part are unsubstituted or substituted by one to three radicals $R^y$:

$R^y$ is cyano, nitro, halogen, hydroxyl, amino, aminocarbonyl, aminothiocarbonyl, $C_1$-$C_6$-alkyl, $C_1$-$C_6$-haloalkyl, $C_1$-$C_6$-alkylsulfonyl, $C_1$-$C_6$-alkyl-sulfoxyl, $C_3$-$C_6$-cycloalkyl, $C_1$-$C_6$-alkoxy, $C_1$-$C_6$-haloalkoxy, $C_1$-$C_6$-alkoxy-carbonyl, $C_1$-$C_6$-alkylthio, $C_1$-$C_6$-alkylamino, di-$C_1$-$C_6$-alkylamino, $C_1$-$C_6$-alkylaminocarbonyl, di-$C_1$-$C_6$-alkylaminocarbonyl, $C_1$-$C_6$-alkylamino-thiocarbonyl, di-$C_1$-$C_6$-alkylaminothiocarbonyl, $C_2$-$C_6$-alkenyl, $C_2$-$C_6$-alkenyloxy, $C_3$-$C_6$-cyclo-alkyl, $C_3$-$C_6$-cycloalkenyl, phenyl, phenoxy, phenylthio, benzyl, benzyloxy, 5- or 6-membered heterocyclyl, 5- or 6-membered hetaryl, 5- or 6-membered hetaryloxy or C(=NOR$^\alpha$)—OR$^\beta$;

$R^\alpha, R^\beta$ are hydrogen or $C_1$-$C_6$-alkyl;

$R^a$ and $R^b$ together, via an alkylene or alkenylene chain with the bridging atom, may also form a saturated or unsaturated 5- or 6-membered ring;

$R^3$ is hydrogen, halogen, cyano, $C_1$-$C_6$-alkyl, $C_1$-$C_6$-haloalkyl, $C_1$-$C_6$-alkoxy, $C_1$-$C_6$-haloalkoxy or $C_3$-$C_8$-alkenyloxy;

$R^4$ is hydrogen, halogen, cyano, hydroxyl, mercapto, azido, $C_1$-$C_6$-alkyl, $C_2$-$C_8$-alkenyl, $C_2$-$C_8$-alkynyl, $C_1$-$C_6$-haloalkyl, $C_1$-$C_6$-alkoxy, $C_3$-$C_8$-alkenyloxy, $C_3$-$C_8$-alkynyloxy, $C_1$-$C_6$-haloalkoxy, $C_1$-$C_6$-alkylthio, $C_3$-$C_8$-alkenylthio, $C_3$-$C_8$-alkynylthio, $C_1$-$C_6$-haloalkylthio, —ON=CR$^a$R$^b$, —CR$^c$=NOR$^a$, —NR$^c$N=CR$^a$R$^b$, —NR$^a$R$^b$, —NR$^c$NR$^a$R$^b$, —NOR$^a$, —NR$^c$C(=NR$^c$)NR$^a$R$^b$, —NR$^c$C(=O)NR$^a$R$^b$, —NR$^a$C(=O)R$^c$, —NR$^a$C(=NOR$^c$)R$^{c'}$, —OC(=O)R$^c$, —C(=NOR$^c$)NR$^a$R$^b$, —CR$^c$(=NNR$^a$R$^b$), —C(=O)NR$^a$R$^b$or —C(=O)R$^c$;

$R^c$ is one of the monovalent groups mentioned under $R^a$ and $R^b$;

x is halogen, $C_1$-$C_6$-alkyl, $C_1$-$C_6$-alkoxy or $C_1$-$C_6$-haloalkyl; and m is an integer from 1 to 5.

Moreover, the invention relates to processes for preparing these compounds, to compositions comprising them and to their use for controlling harmful fungi.

Pyridylpyrimidine derivatives having fungicidal action are known from EP-A 407 899, DE-A 42 27 811 and WO-A 92/10490. Tetrahydropyrimidine derivatives having fungicidal action are known from GB-A 2 277 090.

The compounds described in the abovementioned publications are suitable for use as crop protection agents against harmful fungi.

However, in many cases their activity is unsatisfactory.

It is an object of the present invention to provide compounds having improved activity.

We have found that this object is achieved by the phenylpyrimidine derivatives I defined at the outset. Moreover, we have found processes for their preparation and compositions comprising them for controlling harmful fungi and their use for this purpose.

Compared to the prior-art compounds, the compounds of the formula I have increased activity against harmful fungi.

The compounds I can be obtained by different routes.

To prepare compounds of the formula I in which $R^4$ is cyano or a group bound via a heteroatom, the starting materials used are advantageously sulfones of the formula II. In the formula II, the substituents $X_m$ and $R^1$ to $R^3$ are as defined in formula I and R is $C_1$-$C_4$-alkyl, preferably methyl.

The sulfones of the formula II are reacted under basic conditions with compounds of the formula III. For practical reasons, it is alternatively possible to employ directly the alkali metal, alkaline earth metal or ammonium salt of the compound III.

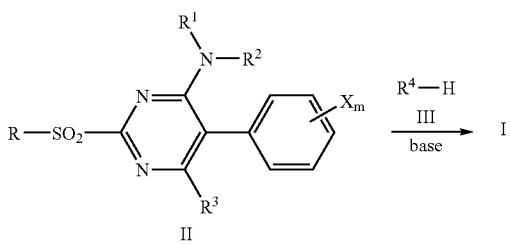

This reaction is usually carried out at temperatures of from 25° C. to 250° C., preferably from 40° C. to 210° C., in an inert organic solvent in the presence of a base [cf. DE-A 39 01 084; Chimia, 50, 525-530 (1996); Khim. Geterotsikl. Soedin, 12 1696-1697(1998).

Suitable solvents are halogenated hydrocarbons, ethers, such as diethyl ether, diisopropyl ether, tert-butyl methyl ether, 1,2-dimethoxyethane, dioxane, anisole and tetrahydrofuran, and also dimethyl sulfoxide, dimethylformamide and dimethylacetamide. Particular preference is given to ethanol, dichloromethane, acetonitrile and tetrahydrofuran. It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal hydrides, such as lithium hydride, sodium hydride, potassium hydride and calcium hydride, and alkali metal and alkaline earth metal carbonates, such as lithium carbonate, potassium carbonate and calcium carbonate. The bases are generally employed in catalytic amounts; however, they can also be employed in excess.

The starting materials are generally reacted with one another in equimolar amounts. In terms of yield, it may be advantageous to employ an up to 10-fold excess, in particular up to 3-fold excess, of III, based on II.

Compounds of the formula I in which $R^4$ is hydrogen, alkyl, alkenyl, alkynyl or haloalkyl are advantageously obtained from phenylmalonic esters of the formula IV by reaction with amidines of the formula V.

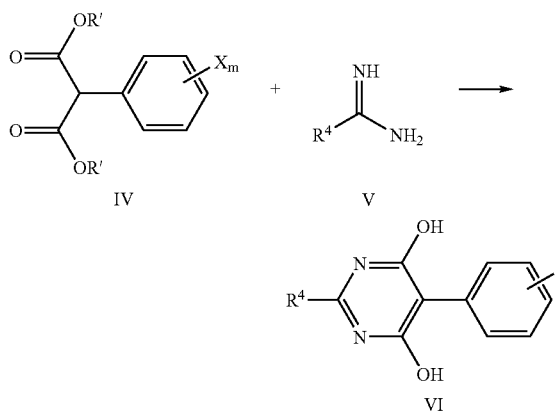

This reaction is advantageously carried out under the conditions known from J. Chem. Soc. (1943) 388 and J. Org. Chem. 17 (1952), 1320.

Phenylmalonic esters of the formula IV are known from EP-A 10 02 788.

Hydroxypyrimidines of the formula VI are converted into halogen compounds VII [cf. J. Chem. Soc. (1943) 383; Helv. Chim. Acta 64 (1981), 113-152]. Suitable halogenating agents are in particular $POCl_3$ and $POBr_3$.

The halopyrimidines VII give, by reaction with amines VIII, compounds of the formula I.

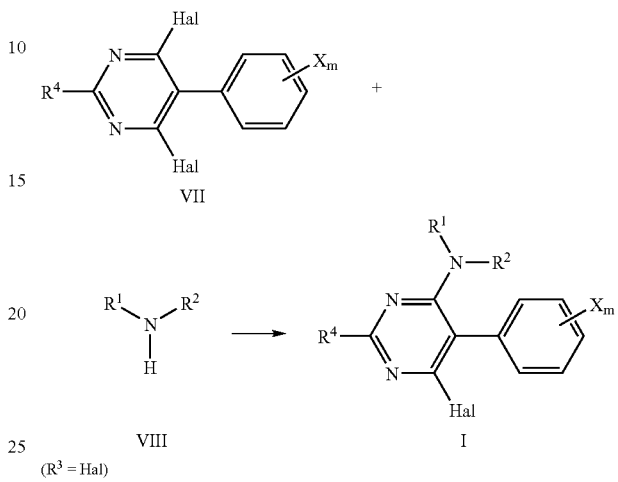

This reaction is advantageously carried out under J. Chem. Soc. (1943) 383 and Chem. Eur. J. 5 (12) (1999), 3450-3458.

Phenylpyrimidines of the formula I in which $R^3$ is cyano or a group attached via oxygen are advantageously obtained from the corresponding halogen compounds of the formula I by reaction with compounds IX under basic conditions. For practical reasons, it is alternatively possible to employ directly the alkali metal, alkaline earth metal or ammonium salt of the compound IX.

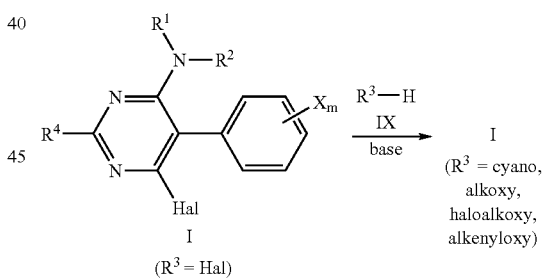

This reaction is usually carried out at temperatures of from 25° C. to 250° C., preferably from 40° C. to 210° C., in an inert organic solvent, if appropriate in the presence of a base [cf. Recl. Trav. Chim. Pays-Bas 61 (1942), 291; J. Heterocycl. Chem. 30 (4) (1993), 993-995].

Suitable solvents are ethers, sulfoxides, amides, particularly preferably dimethyl sulfoxide, N,N-dimethylformamide, N-methylpyrrolidone, N,N-dimethylacetamide, diethyl ether, tetrahydrofuran and 1,2-dimethoxyethane. It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal hydrides, such as lithium hydride, sodium hydride, potassium hydride and calcium hydride, and alkali metal and alkaline earth metal carbonates, such as lithium carbonate, potassium carbonate and calcium carbonate.

The bases are generally employed in catalytic amounts; however, they can also be employed in excess.

Phenylpyrimidines of the formula I in which $R^3$ is $C_1$-$C_6$-alkyl or $C_1$-$C_6$-haloalkyl are advantageously obtained from the corresponding halogen compounds of the formula I by reaction with organometallic compounds of the formula X in which M is a group Mg-Hal, Zn-$R^3$ or B(OR)$_2$, where Hal is a halogen atom and R is hydrogen or $C_1$-$C_4$-alkyl and $R^3$ is $C_1$-$C_6$-alkyl.

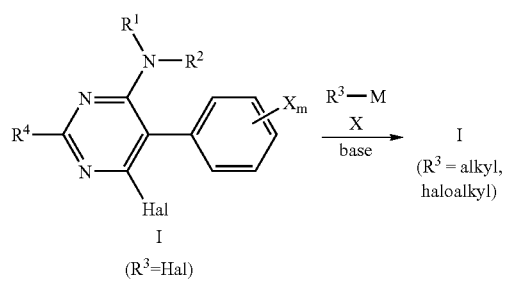

This reaction is usually carried out at temperatures of from −25° C. to 250° C., preferably from 0° C. to 150° C., in an inert organic solvent, if appropriate in the presence of a transition metal catalyst [vgl. Chem. and Pharm. Bull. 28 (2) (1980), 571-577; Tetrahedron Lett. 37 (8) (1996), 1309; Tetrahedron Lett. 35 (19) (1994), 3155; Synlett 7 (1999), 1145].

Suitable solvents are aliphatic hydrocarbons, aromatic hydrocarbons and ethers, particularly preferably diethyl ether, tetrahydrofuran, 1,2-dimethoxyethane, benzene, toluene and xylene. It is also possible to use mixtures of the solvents mentioned.

Suitable transition metal catalysts are iron, cobalt, nickel, rhodium, platinum or palladium compounds, in particular nickel(0), nickel(II), palladium(0) and palladium(II) compounds. It is possible to use salts, such as palladium chloride or palladium acetate, or else Pd complexes. The only condition is that the palladium ligands can be replaced by the substrate under the reaction conditions.

The starting materials are generally reacted with one another in equimolar amounts. In terms of yield, it may be advantageous to employ an up to 10-fold, in particular up to 3-fold, excess of X, based on I.

The starting materials of the formula II required for preparing the compounds I can be obtained by methods known from the literature, for example by the following synthesis route:

starting from phenylmalonic acid alkyl esters of the formula XI and thiourea, compounds of the formula XII are obtained

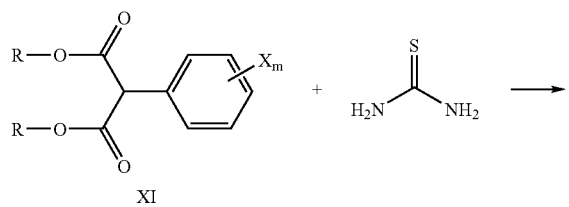

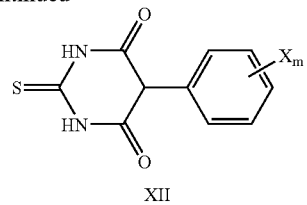

where in formula XI R is $C_1$-$C_6$-alkyl. The reaction is usually carried out in a protic solvent, such as, for example, an alcohol, in particular ethanol, if appropriate in the presence of a base such as Na$_2$CO$_3$ or NaHCO$_3$. The reaction temperature is preferably 70-220° C. [cf. Collect. Czech. Chem. Commun. 48 (1983), 137-143; Heteroat. Chem. 10 (1999), 17-23; Czech. Chem. Commun. 58 (1993), 2215-2221].

The required phenylmalonic acid esters XI are known from EP-A 10 02 788.

Using alkylating agents XIII, compounds XII are converted into thiobarbituric acid derivatives. In the formula XIII, R is $C_1$-$C_6$-alkyl and X is a nucleophilically displaceable leaving group. Formula XIII represents, in a general manner, customary alkylating agents, such as methyl chloride and methyl bromide, dimethyl sulfate or methyl methanesulfonate.

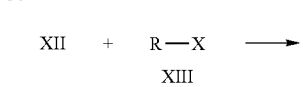

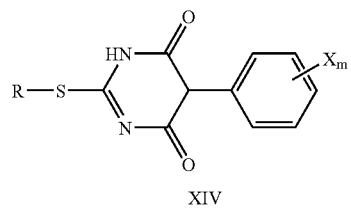

The reaction can be carried out in water or else in a dipolar aprotic solvent, such as, for example, N,N-dimethylformamide [cf. U.S. Pat. No. 5,250,689]; it is preferably carried out in the presence of a base, such as, for example, KOH, NaOH, NaHCO$_3$ and Na$_2$CO$_3$ or pyridine. The reaction temperature is preferably 10-60° C.

Compounds XIV are converted into dichloropyrimidines of the formula XV [cf. EP-A 745 593; WO-A 99/32458; J.Org. Chem. 58 (1993), 3785-3786].

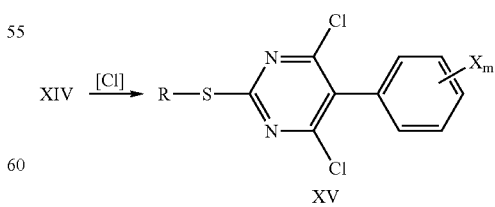

Suitable chlorinating agents [Cl] are, for example, POCl$_3$, PCl$_3$/Cl$_2$ or PCl$_5$. The reaction can be carried out in excess chlorinating agent (POCl$_3$) or in an inert solvent. This reaction is usually carried out at from 10 to 180° C.

By amination with XVI, the dichloro compounds of the formula XV are converted into the compounds of the formula XVII.

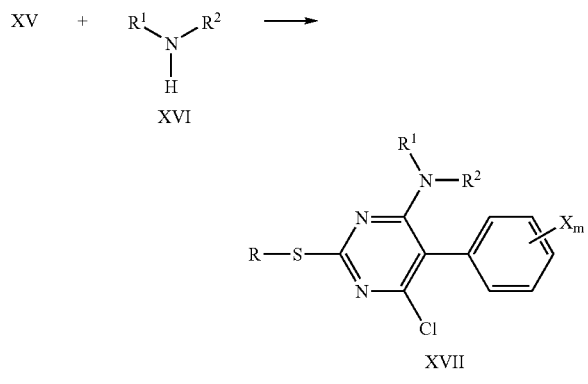

This reaction is preferably carried out at from 20 to 120° C. [cf. J. Chem. Res. S (7) (1995), 286-287; Liebigs Ann. Chem. (1995), 1703-1705] in an inert solvent, if appropriate in the presence of an auxiliary base, such as $NaHCO_3$, $Na_2CO_3$ or tert.amines.

The amines of the formula XVI are commercially available or known from the literature, or they can be prepared by known methods.

The thio compounds XVII are oxidized to the sulfones of the formula II.

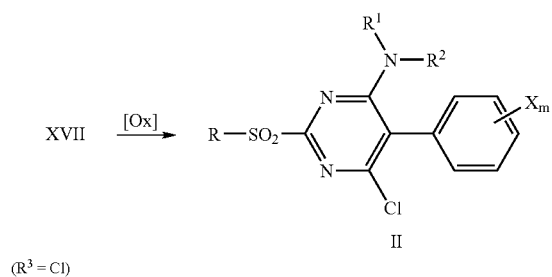

The reaction is preferably carried out at from 10 to 50° C. in the presence of protic or aprotic solvents [cf.: B. Kor. Chem. Soc. 16 (1995), 489-492; Z. Chem. 17 (1977), 63]. Suitable oxidizing agents are, for example, hydrogen peroxide or 3-chloroperbenzoic acid.

The introduction of groups $R^3$ different from chlorine into the sulfones II can be carried out analogously to the compounds of the formula I.

Compounds of the formula I in which $R^4$ is —C(=O)$R^c$, —C(=O)$NR^aR^b$, —C(=NOR$^c$)$NR^aR^b$, —C(=NNR$^a$R$^b$)$R^c$ or —C(=NOR$^a$)$R^c$ are advantageously obtained from compounds of the formula I in which $R^4$ is cyano.

Compounds of the formula I in which $R^4$ is —C(=O) $NR^aR^b$ or —C(=NOR$^c$)$NR^aR^b$ are from the corresponding nitriles ($R^4$ =cyano) by hydrolysis under acidic or basic conditions to give the carboxylic acids of the formula Ia and amidation with amines HNR$^a$R$^b$. Hydrolysis is usually carried out in inert polar solvents, such as water or alcohols, preferably using inorganic bases, such as alkali metal or alkaline earth metal hydroxides, in particular NaOH.

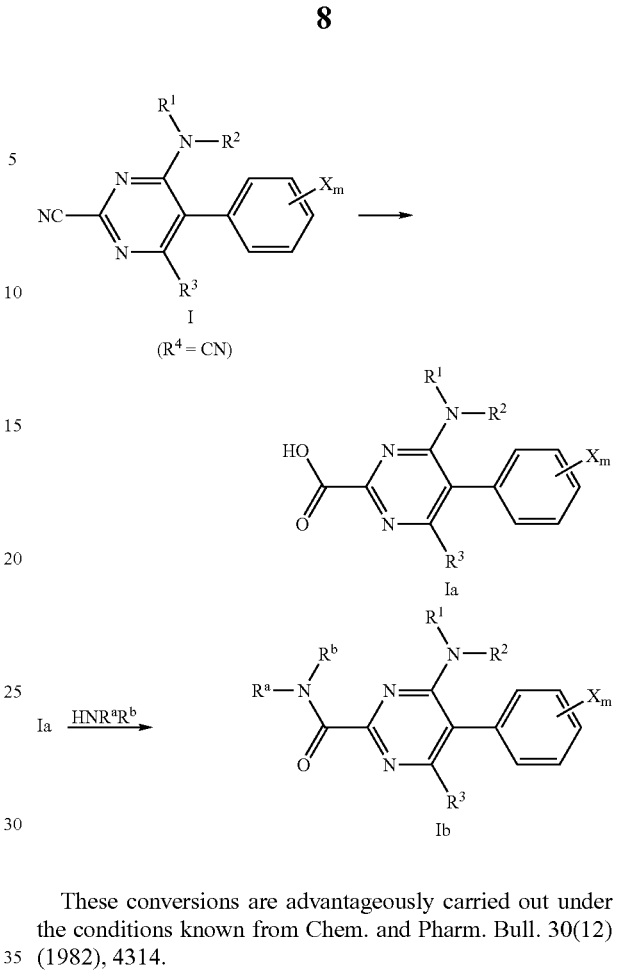

These conversions are advantageously carried out under the conditions known from Chem. and Pharm. Bull. 30(12) (1982), 4314.

Compounds of the formula I in which $R^4$ is —C(=NOR$^c$)NR$^a$R$^b$ are obtained from amides of the formula Ib by oximation with substituted hydroxylamines $H_2N$—OR$^c$ under basic conditions [cf. U.S. Pat. No. 4,876,252]. The substituted hydroxylamines can be used as free base or, preferably, in the form of their acid addition salts. Particularly suitable are, for practical reasons, the halides, such as the chlorides, or the sulfates.

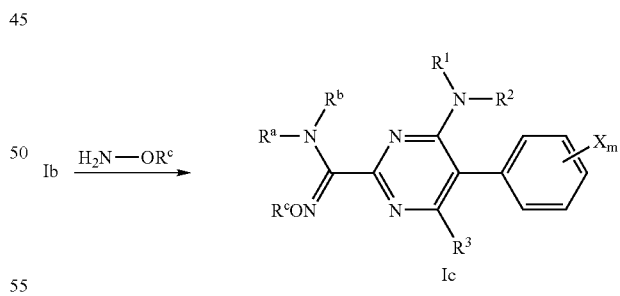

Alternatively, the amidoximes of the formula Ic in which $R^a$ and $R^b$ are hydrogen can also be obtained from the corresponding nitriles ($R^4$=cyano) by reaction with hydroxylamine and subsequent alkylation. This reaction is advantageously carried out under the conditions known from DE-A 198 37 794.

Compounds of the formula I in which $R^4$ is —C(=O)$R^c$ can be obtained from the corresponding nitriles ($R^4$=cyano) by reaction with Grignard reagents $R^c$-Mg-Hal where Hal is a halogen atom, in particular chlorine or bromine.

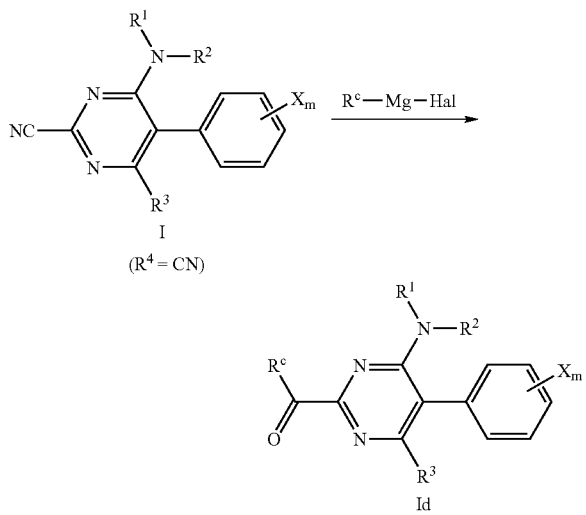

This reaction is advantageously carried out under the conditions known from J. Heterocycl. Chem. 31(4) (1994), 1041.

The substituents and indices in formulae Ia, Ib and Ic correspond to those in formula I.

Compounds of the formula I in which $R^4$ is $—C(=NNR^aR^b)R^c$ can be obtained via the carbonyl compounds Id. They are obtained by reacting Id with hydrazines $H_2NNR^aR^b$, preferably under the conditions known from J. Org. Chem. 31 (1966), 677.

Compounds of the formula I in which $R^4$ is $—C(=NOR^a)R^c$ can be obtained by oximating carbonyl compounds Id. The oximation of Id is carried out analogously to the oximation of the compounds Ib.

The reaction mixtures are worked up in a customary manner, for example by mixing with water, separating the phases and, if appropriate, chromatographic purification of the crude products. Some of the intermediates and end products are obtained in the form of colorless or slightly brownish, viscous oils which can be purified or freed from volatile components under reduced pressure and at moderately elevated temperature. If the intermediates and end products can be obtained as solids, purification can also be carried out by recrystallization or digestion.

If individual compounds I are not obtainable by the routes described above, they can be prepared by derivatization of other compounds I.

In the definitions of the symbols given in the above formulae, collective terms were used which generally represent the following substituents:

halogen: fluorine, chlorine, bromine and iodine;

alkyl: saturated, straight-chain or branched hydrocarbon radicals having 1 to 4 or 6 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 6 carbon atoms (as mentioned above), where in these groups some or all of the hydrogen atoms can be replaced by halogen atoms as mentioned above, for example $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 10 carbon atoms (as mentioned above) which are attached to the skeleton via an oxygen atom (—O—);

alkylthio: straight-chain or branched alkyl groups having 1 to 10 or 1 to 4 carbon atoms (as mentioned above) which are attached to the skeleton via a sulfur atom (—S—);

alkenyl: unsaturated, straight-chain or branched hydrocarbon radicals having 2 to 4, 6 or 8 carbon atoms and a double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

haloalkenyl: unsaturated, straight-chain or branched hydrocarbon radicals having 2 to 8 carbon atoms and a double bond in any position (as mentioned above), where in these groups some or all of the hydrogen atoms may be replaced by halogen atoms as mentioned above, in particular by fluorine, chlorine or bromine;

alkynyl: straight-chain or branched hydrocarbon groups having 2 to 4, 6 or 8 carbon atoms and a triple bond in any position, for example $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3- dimethyl-1-butynyl, 1-ethyl-2-butynyl, 1-ethyl-3-butynyl, 2-ethyl-3-butynyl and 1-ethyl-1-methyl-2-propynyl;

haloalkynyl: unsaturated, straight-chain or branched hydrocarbon radicals having 2 to 8 carbon atoms and a triple bond in any position (as mentioned above), where in these groups some or all of the hydrogen atoms may be replaced by halogen atoms as mentioned above, in particular by fluorine, chlorine or bromine;

alkynyloxy: unsaturated, straight-chain or branched hydrocarbon radicals having 3 to 8 carbon atoms and a triple bond in any position which is not adjacent to the heteroatom (as mentioned above), which are attached to the skeleton via an oxygen atom (—O—);

cycloalkyl: monocyclic, saturated hydrocarbon groups having 3 to 6, 8 or 10 carbon ring members, for example $C_3$-$C_8$-cycloalkyl such as cyclopropyl, cyclobutyl, cyclopentyl, cyclohexyl, cycloheptyl and cyclooctyl;

5- or 6-membered heterocyclyl containing, in addition to carbon ring members, one to three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydro-pyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydro- pyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydro-oxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetra-hydropyranyl, 2-tetrahydrothienyl, 3-hexahydropyridazinyl, 4-hexahydropyridazinyl, 2-hexahydropyrimidinyl, 4-hexahydro-pyrimidinyl, 5-hexahydropyrimidinyl, 2-piperazinyl, 1,3,5-hexa-hydrotriazin-2-yl and 1,2,4-hexahydrotriazin-3-yl;

5- or 6-membered heteroaryl which, in addition to carbon ring members, may contain heteroatoms from the group consisting of oxygen, sulfur and nitrogen: aryl as mentioned above or mono- or bicyclic heteroaryl, for example 5-membered heteroaryl which contains one to four nitrogen atoms or one to three nitrogen atom and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered heteroaryl which contains one to three nitrogen atoms or one nitrogen atom and one oxygen or sulfur atom: 5-membered heteroaryl groups which, in addition to carbon atoms, contain one to four nitrogen atoms or one.to three nitrogen atoms and one sulfur or oxygen atom as ring members and in which two adjacent carbon ring members or one nitrogen and one adjacent carbon ring member may be bridged by a buta-1,3-dien-1,4-diyl group;

6-membered heteroaryl which contains one to three or one to four nitrogen atoms: 6-membered heteroaryl groups which, in addition to carbon ring members, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

alkylene: divalent unbranched chains of 1 to 4 $CH_2$ groups, for example $CH_2$, $CH_2CH_2$, $CH_2CH_2CH_2$ and $CH_2CH_2CH_2CH_2$;

oxyalkylene: divalent unbranched chains of 2 to 4 $CH_2$ groups, where one valency is attached to the skeleton via an oxygen atom, for example $OCH_2CH_2$, $OCH_2CH_2CH_2$ and $OCH_2CH_2CH_2CH_2$;

oxyalkyleneoxy: divalent unbranched chains of 1 to 3 $CH_2$ groups, where both valencies are attached to the skeleton via an oxygen atom, for example $OCH_2O$, $OCH_2CH_2O$ and $OCH_2CH_2CH_2O$;

alkenylene: divalent unbranched chains of 1 to 3 $CH_2$ groups and one CH=CH group in any position, for example CH=CHCH$_2$, CH$_2$CH=CHCH$_2$, CH=CHCH$_2$CH$_2$, CH$_2$CH=CHCH$_2$CH$_2$ and CH=CHCH$_2$CH$_2$CH$_2$.

With a view to the intended use of the phenylpyrimidines of the formula I, the following meanings of the substituents are particularly preferred, in each case on their own or in combination:

Preference is given, in particular, to compounds I in which $R^1$ is hydrogen.

Particular preference is likewise given to compounds I in which $R^1$ and $R^2$ independently of one another are $C_1$-$C_6$-alkyl, $C_1$-$C_6$-haloalkyl, $C_3$-$C_6$-cycloalkyl or $C_2$-$C_6$-alkenyl.

Particular preference is given to compounds of the formula I in which $R^1$ is $C_1$-$C_4$-alkyl and $R^2$ is hydrogen.

Particular preference is given to compounds I in which $R^1$ and $R^2$ together with the bridging nitrogen atom form a saturated or unsaturated 5- or 6-membered ring which may be interrupted by an ether (—O—), thio (—S—), sulfoxyl (—S[=O]—) or sulfonyl (—SO$_2$—) group and/or which may be substituted by one or two methyl or halomethyl groups or in which two adjacent carbon atoms are bridged by a methylene group. Substitution by one or two methyl or halomethyl groups, in particular one or two methyl groups, is particularly preferred.

Moreover, preference is given to compounds of the formula I in which $R^1$ and $R^2$ together form a butylene, pentylene or a pentenylene chain which may be substituted by an alkyl group, in particular a methyl group or in which two adjacent carbon atoms may be bridged by a methylene group.

Preference is furthermore given to compounds of the formula I in which $R^1$ and $R^2$ together form a pentylene or pentenylene chain which is substituted by a methyl group.

Particular preference is given to compounds I in which $R^1$ and $R^2$ together with the bridging nitrogen atom form a 3- or 4-methyl-piperidinyl group or a 2-methylpyrrolidine group.

In addition, particular preference is given to compounds I in which $R^3$ is halogen, in particular chlorine.

Particular preference is likewise given to compounds I in which $R^4$ is hydrogen, cyano, azido, $C_1$-$C_6$-alkyl, $C_2$-$C_8$-alkenyl, $C_2$-$C_8$-alkynyl, $C_1$-$C_6$-haloalkyl, —ON=$CR^aR^b$ or —$NR^cN$=$CR^aR^b$ or —C(=$NOR^c$)$NR^aR^b$.

Particular preference is given to compounds I in which $R^4$ is cyano, —$CR^aNOR^b$ or —ON=$CR^aR^b$, in particular –ON=$CR^aR^b$.

In addition, preference is given to compounds I in which $R^4$ is —NH(=NH)$NHR^c$, —NHC(=O)$NHR^a$, —NHC(=O)$R^a$, —OC(=O)$R^a$, —C(=$NOR^c$)$NH_2$ or —$CR^c$(=$NNR^aR^b$).

Furthermore, preference is given to compounds I in which $R^4$ is —$NR^cN$=$CR^aR^b$.

Likewise, preference is given to compounds I in which $R^4$ is —C(=$NOR^c$)$NR^aR^b$, in particular —C(=$NOR^c$)$NH_2$.

In addition, particular preference is given to compounds I in which $R^4$ is $C_1$-$C_6$-alkenyl or azido.

Moreover, preference is given to compounds I in which $R^a$ and $R^b$ are identical or different and are hydrogen, $C_1$-$C_6$-alkyl, $C_1$-$C_4$-alkoxy, phenyl or a five- or six-membered aromatic heterocycle, where the rings may be substituted by one to three groups $R^x$; among these, particular preference is given to the meanings hydrogen, alkyl, alkoxy and unsubstituted or substituted phenyl.

Particularly preferred embodiments of radicals $R^a$ and $R^b$ are $C_1$-$C_4$-alkyl, $C_1$-$C_2$-haloalkyl, $C_1$-$C_4$-alkoxy-$C_1$-$C_2$-alkyl, $C_3$-$C_6$-alkenyl, $C_3$-$C_6$-haloalkenyl, $C_1$-$C_4$-alkoxy, $C_1$-haloalkoxy, pyridyl, pyrazolyl, phenyl or benzyl, or $R^a$ and $R^b$ together form a butylene or pentylene chain, where the cyclic groups may be substituted by up to four substituents selected from the group consisting of halogen, $C_1$-$C_4$-alkyl, $C_1$-haloalkyl, $C_1$-$C_4$-alkoxy and/or $C_1$-$C_4$-alkoxy-$C_1$-$C_2$-alkyl.

A preferred embodiment of $R^c$ is hydrogen.

Preference is likewise given to compounds I in which X is chlorine, fluorine, methyl, trifluoromethyl or methoxy.

Moreover, particular preference is given to compounds I in which one or two substituents X are located in the position ortho to the point of attachment of the pyrimidine ring.

In addition, particular preference is given to compounds IA

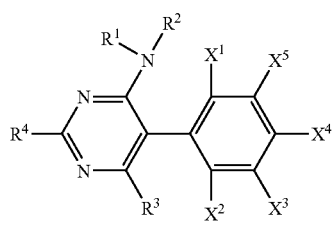

IA in which $R^1$ to $R^4$ are as defined for formula I and $X^1$ to $X^5$ are identical or different and $X^1$ is fluorine, chlorine, $C_1$-$C_4$-alkyl, $C_1$-$C_2$-haloalkyl or $C_1$-$C_4$-alkoxy; and $X^2$,$X^3$,$X^4$,$X^5$ are hydrogen or one of the groups mentioned under $X^1$.

Particular preference is given to compounds IA in which $X^1$,$x^2$ are fluorine, chlorine, methyl, trifluoromethyl or methoxy;

$X^3$,$X^4$,$X^5$ are hydrogen or one of the groups mentioned under $X^1$ and $X^2$.

Moreover, particular preference is given to compounds I in which $X_m$, is $F_5$, 2-Cl, 2-F, 2-$CH_3$, 2-$OCH_3$, 2,6-$Cl_2$, 2,6-$F_2$, 2-Cl-6-F, 2-Br-6-F, 2-$CH_3$-4-Cl, 2-$CH_3$-4-F, 2-$CH_3$-5-F, 2-$CH_3$-6-F, 2-$CH_3$-4-$OCH_3$, 2-$CF_3$-4-F, 2-$CF_3$-5-F, 2-$CF_3$-6-F, 2-$CF_3$-4-$OCH_3$, 2-$OCH_3$-6-F, 2,4,6-$Cl_3$, 2,3,6-$F_3$, 2,4,6-$F_3$, 2,4,6-$(CH_3)_3$, 2,6-$F_2$-4-$CH_3$, 2,6-$F_2$-4-$OCH_3$, 2,4-$F_2$-6-$OCH_3$, 2,6-$(CH_3)_2$-4-$OCH_3$ and 2,6-$(CH_3)_2$-4-F.

Particular preference is given to compounds I in which $X_m$ is $F_5$, 2,6-$Cl_2$, 2,6-$F_2$, 2-Cl-6-F, 2-$CH_3$-4-F, 2-$CH_3$-6-F, 2-$CH_3$-4-Cl and 2,4,6-$F_3$.

The compounds I are suitable for use as fungicides. They have outstanding activity against a broad spectrum of phytopathogenic fungi, in particular from the class of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

*Alternaria* species, *Podosphaera* species, *Sclerotinia* species, *Physalospora* canker on vegetables and fruit,

*Botrytis cinerea* (gray mold) on strawberries, vegetables, ornamentals and grapevines,

*Corynespora cassiicola* on cucumbers,

*Colletotrichum* species on fruit and vegetables,

*Diplocarpon rosae* on roses,

*Elsinoe fawcetti* and diaporthe citri on citrus fruits,

*Sphaerotheca* species on cucurbits, strawberries and roses,

*Cercospora* species on groundnuts, sugar beet and aubergines,

*Erysiphe cichoracearum* on cucurbits,

*Leveillula taurica* on peppers, tomatoes and aubergines,

*Mycosphaerella* species on apples and Japanese apricots,

*Gymnosporangium yamadae*, *Leptothyrium pomi*, *Podosphaera leucotricha* and *Gloedes pomigena* on apples,

*Cladosporium carpophilum* on pears and Japanese apricots,

*Phomopsis* species on pears,

*Phytophthora* species on citrus fruits, potatoes, onions, in particular *Phytophthora* infestans on potatoes and tomatoes,

*Blumeria graminis* (powdery mildew) on cereals,

*Fusarium* and *Verticillium* species on various plants,

*Glomerella cingulata* on tea,

*Drechslera* and *Bipolaris* species on cereals and rice,

*Mycosphaerella* species on bananas and groundnuts,

*Plasmopara viticola* on grapevines,

*Personospora* species on onions, spinach and chrysanthemums,

*Phaeoisariopsis* vitis and *Spaceloma ampelina* on grapefruits,

*Pseudocercosporella herpotrichoides* on wheat and barley,
*Pseudoperonospora* species on hops and cucumbers,
*Puccinia* species and *Typhula* species on cereals and lawn,
*Pyricularia oryzae* on rice,
*Rhizoctonia* species on cotton, rice and lawn,
*Stagonospora nodorum* and *Septoria tritici* on wheat,
*Uncinula necator* on grapevines,
*Ustilago* species on cereals and sugar cane, and also
*Venturia* species (scab) on apples and pears.

Moreover, the compounds I are suitable for controlling harmful fungi such as Paecilomyces variotii in the protection of materials (e.g. wood, paper, paint dispersions, fibers and fabrics) and in the protection of stored products.

The compounds I are applied by treating the fungi or the plants, seeds, materials or the soil to be protected against fungal infection, with a fungicidally active amount of the active compounds. Application can be effected both before and after infection of the materials, plants or seeds by the fungi.

In general, the fungicidal compositions comprise from 0.1 to 95, preferably 0.5 to 90, % by weight of active compound.

When used in crop protection, the rates of application are from 0.01 to 2.0 kg of active compound per ha, depending on the nature of the desired effect.

In the treatment of seed, amounts of active compound of from 0.001 to 0.1 g, preferably 0.01 to 0.05 g, are generally required per kilogram of seed.

When used in the protection of materials or stored products, the rate of application of active compound depends on the nature of the field of application and on the desired effect. Rates of application conventionally used in the protection of materials are, for example, from 0.001 g to 2 kg, preferably 0.005 g to 1 kg, of active compound per cubic meter of material treated.

The compounds I can be converted into the customary formulations, e.g. solutions, emulsions, suspensions, dusts, powders, pastes and granules. The use form depends on the particular purpose; in any case, it should ensure a fine and uniform distribution of the compound according to the invention.

The formulations are prepared in a known manner, e.g. by extending the active compound with solvents and/or carriers, if desired using emulsifiers and dispersants, it also being possible to use other organic solvents as auxiliary solvents if the diluent used is water. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly disperse silica, silicates); emulsifiers such as nonionic and anionic emulsifiers (e.g. polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for spreading and dusts can be prepared by mixing or concomitantly grinding the active substances with a solid carrier.

Granules, e.g. coated granules, impregnated granules and homogeneous granules, can be prepared by binding the active compounds to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are in this case employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active compound.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active compound with good adhesion properties (comprises 23% by weight of active compound).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active compound).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active compound).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active compound).

VI. 90 parts by weight of a compound according to the invention are mixed with 10 parts by weight of N-methyl-α-pyrrolidone, which gives a solution which is suitable for use in the form of microdrops (comprises 90% by weight of active compound).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active compound.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

The active compounds can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, they are intended to guarantee the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within substantial ranges. In general, they are from 0.0001 to 10%, preferably from 0.01 to 1%.

The active compounds may also be used successfully in the ultra-low-volume process (ULV), it being possible to apply formulations comprising over 95% by weight of active compound, or even the active compound without additives.

Various types of oils, herbicides, fungicides, other pesticides, or bactericides may be added to the active compounds, if appropriate also just prior to use (tank mix). These agents can be admixed with the agents according to the invention in a weight ratio of 1:10 to 10:1.

In the use form as fungicides, the compositions according to the invention can also be present together with other active compounds, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides, together with which the compounds according to the invention can be used, is intended to illustrate the possible combinations, but not to impose any limitation:

sulfur, dithiocarbamates and their derivatives, such as Iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylene-bis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2-chloro-N-(4'-chlorobiphenyl-2-yl)nicotinamide, 2,4-dichloro-6-(o-chloroanilino)-s-triazine, O,O-diethyl phthalimidophosphonothioate, 5-amino-1-[bis(dimethylamino)-phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)-benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenyl-sulfodiamide, 5-ethoxy-3-trichloromethyl-1,2,3-thiadiazole, 2-thiocyanato-methylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-i-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-methyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3- ethoxycarbonyl-2-thioureido)benzene, 1,2-bis-(3-methoxycarbonyl-2-thioureido)benzene, strobilurins such as methyl E-2-{2-[6-(2-cyanophenoxy)-pyrimidin-4-yloxy]phenyl}-3-methoxyacrylates, (E)-2-(methoxyimino)-N-methyl-2-[α-(2,5-xylyloxy)-o-tolyl]acetamide, {2-[6-(2-chlorophenoxy)-5-fluoropyrimidin-4-yloxy]phenyl}-(5,6-dihydro-1,4,2-dioxazin-3-yl)methanone O-methyloxime, methyl (E)-methoxyimino[α-(o-tolyloxy)-o-tolyl]acetate, (E)-2-(methoxyimino)-N-methyl-2-(2-phenoxyphenyl)acetamide, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide, methyl (E)-3-methoxy-2-{2-[6-(trifluoromethyl)-2-pyridyloxymethyl]phenyl}acrylate, methyl N-{2-[1-(4-chlorophenyl)-1H-pyrazol-3-yloxymethyl]phenyl}-(N-methoxy)carbamate, methyl (E)-methoxyimino-{(E)-α-[1-(α,α,α-trifluoro-m-tolyl)ethylideneaminooxy]-o-tolyl}acetate, anilinopyrimidines such as N-(4,6-dimethylpyrimidin-2-yl)-aniline, N-[4-methyl-6-(1-propynyl)pyrimidin-2-yl]aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamides such as 3-(4-chlorophenyl)-3-(3,4-dimethoxyphenyl)acryloylmorpholine, 3-(4-fluorophenyl)-3-(3,4-dimethozyphenyl)acryloylmorpholide, and a variety of fungicides such as dodecylguanidine acetate, 1-(3-bromo-6-methoxy-2-methylphenyl)-1-(2,3,4-trimethoxy-6-methylphenyl)methanone, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-amino-butyrolactone, DL-N-(2,6-dimethylphenyl)-N-(phenylacetyl)-alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole-5-chloro-2-cyano-4-n-tolylimidazole-1-sulfodimethylamide, 3,5-dichloro-N-(3-chloro-1-ethyl-1-methyl-2-oxopropyl)-4-methylbenzamide.

SYNTHESIS EXAMPLES

With due modification of the starting compounds, the protocols shown in the synthesis examples below were used for obtaining further compounds I. The resulting compounds, together with physical data, are listed in Table 1 below.

Example 1

Preparation of [6-chloro-2-(N'-isopropylidene-hydrazino)-5-(2,4,6-trifluorophenyl)pyrimidine-4-yl]-((S)-1-tri-fluoromethylethyl)amine [I-1]

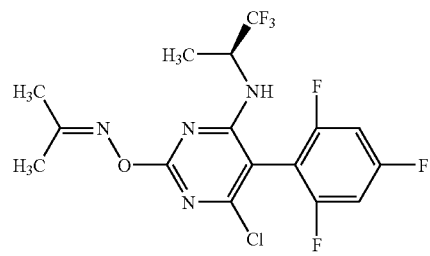

0.16 g (2.2 mmol) of acetone oxime was added to 0.065 g (2.4 mmol) of sodium hydride in 10 ml of dimethylformamide (DMF). The mixture was stirred at 20-25° C. for 1 hour, after which 1.0 g (2.2 mmol) of [6-chloro-2-methanesulfonyl-5-(2,4,6-trifluorophenyl)pyrimidin-4-yl]-((S)-1-trifluoromethylethyl)amine (abbr. sulfone 1) was added. After a further 14 hours of stirring at 20-25° C., the mixture was poured into water and extracted with dichloromethane. The combined organic phases were washed with water, then dried and finally freed from the solvent. This gave 0.6 g of the title compound of m.p. 157-159° C.

Example 2

Preparation of [6-chloro-2-methoxy-5-(2,4,6-trifluorophenyl)pyrimidin-4-yl]-((S)-1-trifluoromethylethyl)amine [I-24]

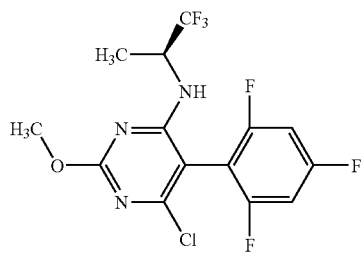

294 mg (1.30 mmol) of sodium methoxide (90% in methanol) were added to a solution of 282 mg (0.65 mmol) of sulfone 1 in 4 ml of anhydrous DMF. The mixture was stirred at 20-25° C. for 16 hours and then diluted with MTBE, washed with water and dried. Distillative removal of the solvent and chromatography on silica gel gave 0.14 g of the title compound of m.p. 121-129° C.

Example 3

Preparation of [6-chloro-2-methylsulfanyl-5-(2,4,6-trifluorophenyl)pyrimidin-4-yl]isopropylamine [I-30]

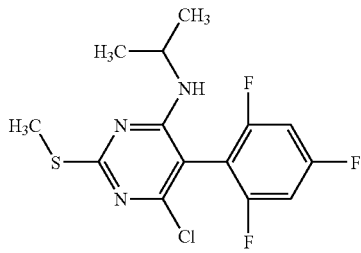

70 mg (1.0 mmol) of sodium thiomethoxide, dissolved in 3 ml of anhydrous THF, were added to a solution of 216 mg (0.5 mmol) of [6-chloro-2-methanesulfonyl-5-(2,4,6-trifluorophenyl)pyrimidin-4-yl]isopropylamine (abbr. sulfone 2) in 2 ml of anhydrous DMF. The mixture was stirred at 20-25° C. for 16 hours and then diluted with MTBE, washed with water and dried. Distillative removal of the solvent and chromatography on silica gel gave 0.21 g of the title compound of m.p. 112-116° C.

Example 4

Preparation of [6-chloro-2-hydrazino-5-(2,4,6-trifluorophenyl)pyrimidin-4-yl]-((S)-1-trifluoromethylethyl)amine

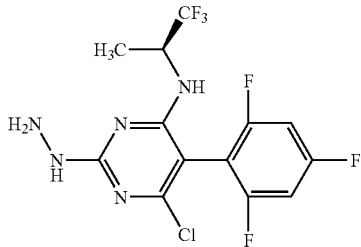

An ethanolic solution of 0.5 g (1.15 mmol) of sulfone 1 and 0.13 g (2.54 mmol) of hydrazine hydrate was stirred at 20-25° C. for 2 hours. The solvent was distilled off and the residue was digested with diisopropyl ether, and the residue was then filtered off and washed with diisopropyl ether/hexane 1:1.

Example 5

Preparation of [6-chloro-2-[N'-(1-trifluoromethylethylidene)hydrazino]-5-(2,4,6-trifluorophenyl)pyrimidin-4-yl]-((S)-1-trifluoromethylethyl)amine [I-56]

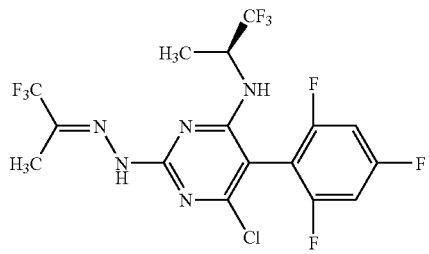

A solution of 0.8 g (2.07 mmol) of the hydrazide from Ex. 4 and 0.28 g (2.49 mmol) of 1,1,1-trifluoroacetone in acetonitrile was stirred at 20-25° C. for 16 hours. The precipitate was filtered off; the filtrate gave, after chromatography on silica gel (CH:MTBE 95:5), 0.3 g of the title compound of m.p. 205-207° C.

Example 6

Preparation of [6-chloro-2-(N-phenylhydrazino)-5-(2,4,6-trifluorophenyl)pyrimidin-4-yl]-((S)-1-trifluoromethylethyl)amine [I-62]

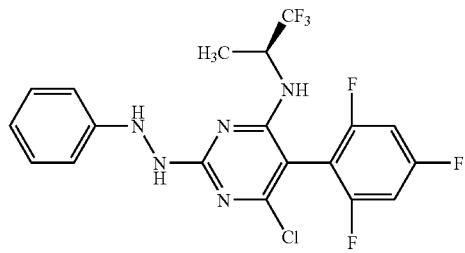

An ethanolic solution of 0.5 g (1.15 mmol) of sulfone 1 and 0.15 g (1.38 mmol) of phenylhydrazine was refluxed for 14 hours. Cooling, distillative removal of the solvent and chromatography on silica gel (cyclohexane:methyl tert-butyl ether [MTBE] 95:5) gave 0.36 g of the title compound.

Example 7

Preparation of [2-azido-6-chloro-5-(2,4,6-trifluorophenyl)pyrimidin-4-yl]-((S)-1-trifluoromethylethyl)amine [I-66]

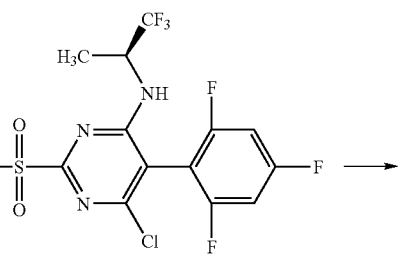

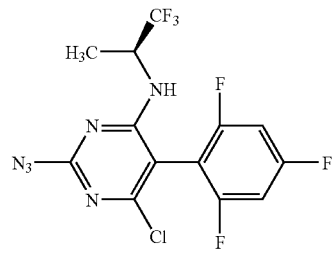

A solution of 0.5 g (1.15 mmol) of sulfone 1 and 0.11 g (1.62 mmol) of sodium azide in acetonitrile was refluxed for 2 hours. Cooling, distillative removal of the solvent and digestion of the residue with water gave 0.33 g of the title compound of m.p. 152-154° C.

Example 8

Preparation of 6-chloro-5-(2-chloro-6-fluorophenyl)-$N^1$-isopropyl-$N^2$-phenylpyrimidine-2,4-diamine [I-69]

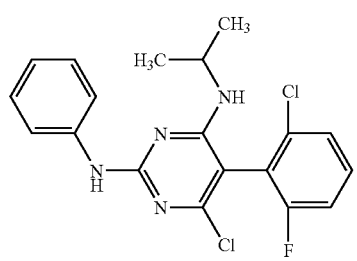

At −70° C., 0.62 g (6.6 mmol) of aniline was added to a suspension of 2.9 g of butyllithium (15% solution in hexane) in 15 ml of tetrahydrofuran [THF], and the mixture was then stirred at −70° C. for 1 hour. 1.0 g (2.64 mmol) of [6-chloro-5-(2-chloro-6-fluorophenyl)-2-methanesulfonylpyrimidin-4-yl]isopropylamine (abbr. sulfone 3) was added, and the mixture was then warmed to 20-25° C. The reaction mixture was poured into ice-water and acidified with hydrochloric acid. The mixture was extracted with 2×40 ml of MTBE, and the combined organic phases gave, after drying and distillative removal of the solvent, 1.0 g of the title compound.

Example 9

Preparation of 4-chloro-6-((S)-1-trifluoromethyl-ethyl-amino)-5-(2,4,6-trifluorophenyl)pyrimidin-2-carbonitrile [I-73]

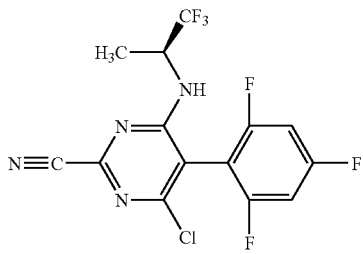

A solution of 0.5 g (1.15 mmol) of sulfone 1 and 0.36 g (2.31 mmol) of tetraethylammonium cyanide in dichloromethane was stirred at 20-25° C. for 20 hours. Distillative removal of the solvent and chromatography on silica gel (cyclohexane [CH]:MTBE 9:1) gave 0.18 g of the title compound of m.p. 134-136° C.

Example 10

Preparation of 4-chloro-5-(2-chloro-6-fluorophenyl)-6-isopropylaminopyrimidine-2-carbonitrile [I-74]

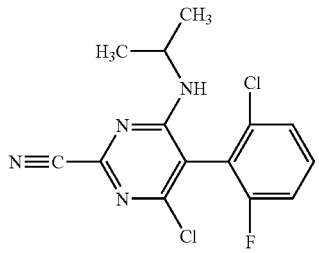

A solution of 1.0 g (2.63 mmol) of sulfone 3 and 0.21 g (3.16 mmol) of potassium cyanide in acetonitrile was stirred at 20-25° C. for 5 days. The solvent was distilled off and the residue was digested with MTBE:ethyl acetate [EA] 9:1. Filtration and concentration of the filtrate gave 0.61 g of the title compound of m.p 186-188° C.

TABLE I

| No. | $R^1$ | $R^2$ | $R^3$ | $R^4$ | $X^1$ | $X^2$ | $X^3$ | $X^4$ | $X^5$ | Phys. data (m.p. [° C.]) |
|---|---|---|---|---|---|---|---|---|---|---|
| I-1 | (S)—CH(CF$_3$)CH$_3$ | H | Cl | —O—N=C(CH$_3$)$_2$ | F | F | H | F | H | 157-159 |
| I-2 | (S)—CH(CF$_3$)CH$_3$ | H | Cl | ⌬=N—O— (cyclopentanone O-methyloxime) | F | F | H | F | H | 88-92 |

TABLE I-continued

| No. | R$^1$ | R$^2$ | R$^3$ | R$^4$ | X$^1$ | X$^2$ | X$^3$ | X$^4$ | X$^5$ | Phys. data (m.p. [° C.]) |
|---|---|---|---|---|---|---|---|---|---|---|
| I-3 | (S)—CH(CF$_3$)CH$_3$ | H | Cl | cyclohexanone O-methyl oxime | F | F | H | F | H | 176-179 |
| I-4 | (S)—CH(CF$_3$)CH$_3$ | H | Cl | —O—N=C(CH$_3$)C$_6$H$_5$ | F | F | H | F | H | 151-155 |
| I-5 | (S)—CH(CF$_3$)CH$_3$ | H | Cl | —ON=C(CH$_3$)—OCH$_2$CH$_3$ | F | F | H | F | H | 110-112 |
| I-6 | (S)—CH(CF$_3$)CH$_3$ | H | Cl | —O—N=CHC$_6$H$_5$ | F | F | H | F | H | 145-146 |
| I-7 | (S)—CH(CF$_3$)CH$_3$ | H | Cl | —O—N=CHCH$_3$ | F | F | H | F | H | 139-141 |
| I-8 | (S)—CH(CF$_3$)CH$_3$ | H | Cl | (CH$_3$)$_3$C—C(CH$_3$)=N—OCH$_3$ | F | F | H | F | H | 350 |
| I-9 | (S)—CH(CF$_3$)CH$_3$ | H | Cl | di(2-pyridyl)C=N—OCH$_3$ | F | F | H | F | H | 84-86 |
| I-10 | (S)—CH(CF$_3$)CH$_3$ | H | Cl | (CH$_3$)$_2$CHCH$_2$—C(CH$_3$)=N—OCH$_3$ | F | F | H | F | H | 68-70 |
| I-11 | (S)—CH(CF$_3$)CH$_3$ | H | Cl | —O—N=CH(2,6-Cl$_2$—C$_6$H$_3$) | F | F | H | F | H | 87-90 |
| I-12 | CH(CH$_3$)$_2$ | H | Cl | —O—CH$_3$ | F | F | H | F | H | 137-139 |
| I-13 | CH(CH$_3$)$_2$ | H | Cl | —O—CH$_3$ | Cl | F | H | H | H | 147-149 |
| I-14 | CH(CH$_3$)$_2$ | H | Cl | —O—CH$_2$CH$_3$ | F | F | H | F | H | oil |
| I-15 | CH(CH$_3$)$_2$ | H | Cl | —O—CH$_2$CH$_3$ | Cl | F | H | H | H | 165-168 |
| I-16 | CH(CH$_3$)$_2$ | H | Cl | —O—CH$_2$CH$_2$CH$_3$ | F | F | H | F | H | oil |
| I-17 | CH(CH$_3$)$_2$ | H | Cl | —O—CH$_2$CH$_2$CH$_3$ | Cl | F | H | H | H | 110-112 |
| I-18 | CH(CH$_3$)$_2$ | H | Cl | —O—CH(CH$_3$)$_2$ | Cl | F | H | H | H | 125-127 |

TABLE I-continued

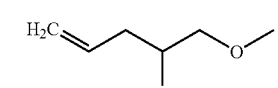

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-19 | (S)—CH(CF₃)CH₃ | H | Cl | —O—CH₂CH₂CH₂CH₃ | F | F | H | F | H | 116-117 |
| I-20 | CH(CH₃)₂ | H | Cl | —O—CH₂CH₂CH₂CH₃ | Cl | F | H | H | H | 98-100 |
| I-21 | CH(CH₃)₂ | H | Cl | —O—C(CH₃)₃ | Cl | F | H | H | H | 118-121 |
| I-22 | CH(CH₃)₂ | H | Cl | —O—CH(CH₃)CH₂CH₃ | Cl | F | H | H | H | 108-111 |
| I-23 | (S)—CH(CF₃)CH₃ | H | Cl | —O—CH(CH₃)CH₂CH₃ | F | F | H | F | H | 129-131 |
| I-24 | (S)—CH(CF₃)CH₃ | H | Cl | —O—CH₃ | F | F | H | F | H | 121-129 |
| I-25 | (S)—CH(CF₃)CH₃ | H | Cl | —O—CH₂CH₃ | F | F | H | F | H | 147-149 |
| I-26 | (S)—CH(CF₃)CH₃ | H | Cl | —O—CH(CH₃)₂ | F | F | H | F | H | 159-161 |
| I-27 | —CH₂CH₂CH(CH₃)CH₂CH₂— | | Cl | —HO | Cl | F | H | H | H | 164-169 |
| I-28 | —CH₂CH₂CH(CH₃)CH₂CH₂— | | Cl | —O—CH₂CH₃ | F | F | H | F | H | oil |
| I-29 | —CH₂CH₂CH(CH₃)CH₂CH₂— | | Cl | H₂C=CH—CH₂—CH(CH₃)—CH₂—O— | F | F | H | F | H | oil |
| I-30 | CH(CH₃)₂ | H | Cl | —S—CH₃ | F | F | H | F | H | 112-116 |
| I-31 | CH(CH₃)₂ | H | Cl | —S—CH₃ | Cl | F | H | H | H | 106-110 |
| I-32 | CH(CH₃)₂ | H | Cl | —S—CH₂CH₃ | F | F | H | F | H | oil |
| I-33 | CH(CH₃)₂ | H | Cl | —S—CH₂CH₃ | Cl | F | H | H | H | 104-108 |
| I-34 | CH(CH₃)₂ | H | Cl | —S—CH₂CH₂CH₃ | F | F | H | F | H | 95-98 |
| I-35 | CH(CH₃)₂ | H | Cl | —S—CH₂CH₂CH₃ | Cl | F | H | H | H | oil |
| I-36 | CH(CH₃)₂ | H | Cl | —S—CH(CH₃)₂ | F | F | H | F | H | oil |
| I-37 | CH(CH₃)₂ | H | Cl | —S—CH(CH₃)₂ | Cl | F | H | H | H | 111-113 |
| I-38 | CH(CH₃)₂ | H | Cl | —S—CH₂CH₂CH₂CH₃ | Cl | F | H | H | H | oil |
| I-39 | CH(CH₃)₂ | H | Cl | —S—C(CH₃)₃ | Cl | F | H | H | H | 94-96 |
| I-40 | CH(CH₃)₂ | H | Cl | —S—CH(CH₃)CH₃CH₂ | F | F | H | F | H | oil |

TABLE I-continued

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-41 | CH(CH₃)₂ | H | Cl | —S—CH(CH₃)CH₂CH₃ | Cl | F | H | H | H | 114-117 |
| I-42 | (S)—CH(CF₃)CH₃ | H | Cl | —S—CH₂CH₃ | F | F | H | F | H | oil |
| I-43 | (S)—CH(CF₃)CH₃ | H | Cl | —S—CH₂CH₂CH₃ | F | F | H | F | H | 68-69 |
| I-44 | (S)—CH(CF₃)CH₃ | H | Cl | —S—CH(CH₃)₂ | F | F | H | F | H | 73-76 |
| I-45 | (S)—CH(CF₃)CH₃ | H | Cl | —S—CH₂CH₂CH₃ | F | F | H | F | H | oil |
| I-46 | (S)—CH(CF₃)CH₃ | H | Cl | —S—C(CH₃)₃ | F | F | H | F | H | oil |
| I-47 | (S)—CH(CF₃)CH₃ | H | Cl | —S—CH(CH₃)CH₂CH₃ | F | F | H | F | H | 64-65 |
| I-48 | CH₂CH=CH₂ | H | Cl | —S—CH₃ | F | H | H | H | H | 124-126 |
| I-49 | CH₂CH₃ | CH₂CH₃ | Cl | —S—CH₃ | F | H | H | H | H | oil |
| I-50 | —CH₂CH₂CH(CH₃)CH₂CH₂— | | Cl | —S—CH₃ | F | H | H | H | H | oil |
| I-51 | CH(CH₃)₂ | H | Cl | —S—CH₃ | F | H | H | H | H | oil |
| I-52 | —CH₂SCH₂CH₂— | | Cl | —S—CH₃ | F | H | H | H | H | oil |
| I-53 | CH₂—Ph | H | Cl | —S—CH₃ | F | H | H | H | H | 135-137 |
| I-54 | (S)—CH(CF₃)CH₃ | H | Cl | —N(CH₃)—N=C(CF₃)CH₃ | F | F | H | F | H | oil |
| I-55 | (S)—CH(CF₃)CH₃ | H | Cl | —N(CH₃)—N=C(CH₃)—C₆H₅ | F | F | H | F | H | oil |
| I-56 | CH(CH₃)₂ | H | Cl | —NH—N=C(CF₃)CH₃ | F | F | H | F | H | 205-207 |
| I-57 | CH(CH₃)₂ | H | Cl | —NH—N=C(CH₃)—C₆H₅ | F | F | H | F | H | 185-187 |
| I-58 | CH(CH₃)₂ | H | Cl | —NH—N=C(CF₃)—C₆H₅ | F | F | H | F | H | 84-87 |
| I-59 | CH(CH₃)₂ | H | Cl | —NH—N=CH—C₆H₅ | F | F | H | F | H | 138-140 |
| I-60 | (S)—CH(CF₃)CH₃ | H | Cl | —N(CH₃)—N=C(CH₃)₂ | F | F | H | F | H | 205-208 |
| I-61 | (S)—CH(CF₃)CH₃ | H | Cl | —N(CH₃)—N=CH—C₆H₅ | F | F | H | F | H | 152-155 |
| I-62 | (S)—CH(CF₃)CH₃ | H | Cl | —NH—NH—C₆H₅ | F | F | H | F | H | oil |

TABLE I-continued

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-63 | (S)—CH(CF₃)CH₃ | H | Cl | 4-chloro-1-methyl-pyrazol-3-yl-NH— | F | F | H | F | H | 132-134 |
| I-64 | (S)—CH(CF₃)CH₃ | H | Cl | —N(CH₃)—NH₂ | F | F | H | F | H | 126-128 |
| I-65 | (S)—CH(CF₃)CH₃ | H | Cl | —NH—NH—CH₂CF₃ | F | F | H | F | H | oil |
| I-66 | (S)—CH(CF₃)CH₃ | H | Cl | —N₃ | F | F | H | F | H | 152-154 |
| I-67 | CH(CH₃)₂ | H | Cl | —N(CH₃)₂ | Cl | F | H | H | H | 91-94 |
| I-68 | CH(CH₃)₂ | H | Cl | —NH—OCH₃ | Cl | F | H | H | H | 151-153 |
| I-69 | CH(CH₃)₂ | H | Cl | —NH—C₆H₅ | Cl | F | H | H | H | oil |
| I-70 | CH(CH₃)₂ | H | Cl | 1,3-dimethyl-pyrazol-4-yl-NH— | Cl | F | H | H | H | oil |
| I-71 | —CH₂CH₂CH(CH₃)CH₂CH₂— | | Cl | —NHCH(CH₃)₂ | Cl | F | H | H | H | 107-109 |
| I-72 | —CH₂CH₂CH(CH₃)CH₂CH₂— | | Cl | —N(CH₂CH₃)₂ | Cl | F | H | H | H | oil |
| I-73 | (S)—CH(CF₃)CH₃ | H | Cl | —CN | F | F | H | F | H | 134-136 |
| I-74 | CH(CH₃)₂ | H | Cl | —CN | Cl | F | H | H | H | 186-188 |
| I-75 | (S)—CH(CF₃)CH₃ | H | Cl | —CH₃ | F | F | H | F | H | 83-85 |
| I-76 | (S)—CH(CF₃)CH₃ | H | Cl | —CH₃ | Cl | F | H | H | H | 87-90 |
| I-77 | CH(CH₃)₂ | CH₃ | Cl | —CH₃ | H | H | F | H | H | 75-77 |
| I-78 | —CH₂CH₂CH(CH₃)CH₂CH₂— | | Cl | —CH₂CH₃ | Cl | F | H | H | H | oil |
| I-79 | —CH₂CH₂CH(CH₃)CH₂CH₂— | | Cl | —CH₂CH=CH₂ | Cl | F | H | H | H | oil |
| I-80 | —CH₂CH₂CH(CH₃)CH₂CH₂— | | Cl | —CH(CH₃)₂ | Cl | F | H | H | H | oil |
| I-81 | (S)—CH(CF₃)CH₃ | H | Cl | —S—CH₃ | F | F | H | F | H | 94-96 |
| I-82 | C(CH₃)CH₂CH₃ | H | Cl | —O—N=C(CH₃)₂ | F | F | H | F | H | 91 |

TABLE I-continued

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-83 | C(CH₃)CH₂CH₃ | H | Cl | cyclopentanone O-methyl oxime | F | F | H | F | H | 180 |
| I-84 | C(CH₃)CH₂CH₃ | H | Cl | cyclohexanone O-methyl oxime | F | F | H | F | H | 157 |
| I-85 | C(CH₃)CH₂CH₃ | H | Cl | —O—N=CH(2, 6-Cl₂—C₆H₃) | F | F | H | F | H | 159 |
| I-86 | C(CH₃)CH₂CH₃ | H | Cl | —CN | F | F | H | F | H | 113-118 |
| I-87 | (R)—C(CH₃)CH₂CH₃ | H | Cl | —CH₃ | F | F | H | OCH₃ | H | oil |
| I-88 | —CH(CH₃)CH₂CH₂— | | Cl | —O—N=C(CH₃)₂ | F | F | H | F | H | oil |
| I-89 | —CH(CH₃)CH₂CH₂— | | Cl | cyclopentanone O-methyl oxime | F | F | H | F | H | oil |
| I-90 | —CH(CH₃)CH₂CH₂— | | Cl | cyclohexanone O-methyl oxime | F | F | H | F | H | oil |
| I-91 | —CH(CH₃)CH₂CH₂— | | Cl | —NH—C(=NH)CH₃ | F | F | H | F | H | oil |
| I-92 | —CH(CH₃)CH₂CH₂— | | Cl | —NH—C(=NH)CH₃ | Cl | F | H | H | H | oil |
| I-93 | —CH(CH₃)CH₂CH₂CH(CH₃)— | | Cl | —NH—C(=NH)CH₃ | F | H | H | CH₃ | H | oil |
| I-94 | —CH(CH₃)CH₂CH₂— | | Cl | —NH—C(=NH)CH₃ | CH₃ | H | H | CH₃ | H | oil |
| I-95 | (R)—C(CH₃)CH(CH₃)₂ | H | Cl | —CN | F | F | H | F | H | 99-105 |
| I-96 | (R)—C(CH₃)CH(CH₃)₂ | H | Cl | —O—N=C(CH₃)₂ | F | F | H | F | H | 120-123 |
| I-97 | (R)—C(CH₃)CH(CH₃)₂ | H | Cl | cyclopentanone O-methyl oxime | F | F | H | F | H | 106-109 |
| I-98 | (R)—C(CH₃)CH(CH₃)₂ | H | Cl | cyclohexanone O-methyl oxime | F | F | H | F | H | 120-123 |
| I-99 | (R)—C(CH₃)CH(CH₃)₂ | H | Cl | —OH | F | F | H | F | H | 84-101 |

TABLE I-continued

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-100 | (R)—C(CH₃)CH(CH₃)₂ | H | Cl | —CN | F | F | H | F | H | 156-158 |
| I-101 | (S)—C(CH₃)CH(CH₃)₂ | H | Cl | —NH—C(=NH)CH₃ | F | F | H | F | H | oil |
| I-102 | (R)—C(CH₃)CH(CH₃)₂ | H | Cl | —O—N=C(CH₃)₂ | Cl | F | H | H | H | oil |
| I-103 | (R)—C(CH₃)CH(CH₃)₂ | H | Cl | cyclopentanone O-methyloxime | Cl | F | H | H | H | oil |
| I-104 | (R)—C(CH₃)CH(CH₃)₂ | H | Cl | cyclohexanone O-methyloxime | Cl | F | H | H | H | oil |
| I-105 | (R)—C(CH₃)CH(CH₃)₂ | H | Cl | —ON=C(CH₃)—OCH₂CH₃ | Cl | F | H | H | H | oil |
| I-106 | (R)—C(CH₃)CH(CH₃)₂ | H | Cl | —ON=CH—C₆H₅ | Cl | F | H | H | H | oil |
| I-107 | (R)—C(CH₃)CH(CH₃)₂ | H | Cl | —O—N=CH(2,6-Cl₂—C₆H₃) | Cl | H | H | F | H | 127 |
| I-108 | (R)—C(CH₃)CH(CH₃)₂ | H | Cl | —CH₃ | F | F | H | OCH₃ | H | oil |
| I-109 | —(CH₂)₅— | | Cl | —O—N=C(CH₃)₂ | F | F | H | F | H | 98-102 |
| I-110 | —(CH₂)₅— | | Cl | cyclopentanone O-methyloxime | F | F | H | F | H | oil |
| I-111 | —(CH₂)₅— | | Cl | cyclohexanone O-methyloxime | F | F | H | F | H | oil |
| I-112 | —(CH₂)₅— | | Cl | N-(4-chlorophenyl)-N'-methylguanidine | F | F | H | F | H | oil |
| I-113 | —(CH₂)₅— | | Cl | —NH—C(=O)CH₃ | F | F | H | F | H | 123-125 |
| I-114 | CH(CH₂CH₃)₂ | H | Cl | —ON=C(CH₃)₂ | F | F | H | F | H | 133 |
| I-115 | CH(CH₂CH₃)₂ | H | Cl | cyclopentanone O-methyloxime | F | F | H | F | H | 155 |

TABLE I-continued

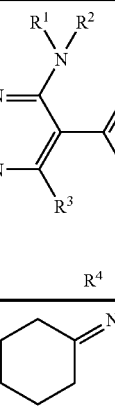

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-116 | CH(CH₂CH₃)₂ | H | Cl | cyclohexanone O-methyl oxime | F | F | H | F | H | 146 |
| I-117 | CH(CH₂CH₃)₂ | H | Cl | —CN | F | F | H | F | H | 126-129 |
| I-118 | —(CH₂)₃CH(CH₃)CH₂— | | Cl | —ON=C(CH₃)₂ | F | F | H | F | H | oil |
| I-119 | —(CH₂)₃CH(CH₃)CH₂— | | Cl | cyclopentanone O-methyl oxime | F | F | H | F | H | oil |
| I-120 | —(CH₂)₃CH(CH₃)CH₂— | | Cl | cyclohexanone O-methyl oxime | F | F | H | F | H | oil |
| I-121 | —(CH₂)₃CH(CH₃)CH₂— | | Cl | —CN | F | F | H | F | H | 107-109 |
| I-122 | —(CH₂)₃CH(CH₃)CH₂— | | Cl | —CH₃ | F | F | H | F | H | oil |
| I-123 | —(CH₂)₂SO₂(CH₂)₂— | | Cl | —O—N=C(CH₃)₂ | F | F | H | F | H | 141-149 |
| I-124 | —(CH₂)₂SO₂(CH₂)₂— | | Cl | cyclopentanone O-methyl oxime | F | F | H | F | H | 179-188 |
| I-125 | —(CH₂)₂SO₂(CH₂)₂— | | Cl | cyclohexanone O-methyl oxime | F | F | H | F | H | 181-191 |
| I-126 | —(CH₂)₂SO₂(CH₂)₂— | | Cl | —(CH₂)₂CH(CH₃)(CH₂)₂— | F | F | H | F | H | oil |
| I-127 | —(CH₂)₂CH=CHCH₂— | | Cl | 4-methyl-2-pentanone O-methyl oxime | F | F | H | F | H | oil |
| I-128 | —(CH₂)₂CH=CHCH₂— | | Cl | cyclopentanone O-methyl oxime | F | F | H | F | H | oil |
| I-129 | —(CH₂)₂CH=CHCH₂— | | Cl | cyclohexanone O-methyl oxime | F | F | H | F | H | oil |
| I-130 | —(CH₂)₂CH=CHCH₂— | | Cl | CN | F | F | H | F | H | 89-98 |

TABLE I-continued

Structure: pyrimidine with R¹R²N- at 4-position, R³ at 6-position, R⁴ at 2-position, and a phenyl ring at 5-position substituted with X¹-X⁵.

| No. | R¹ | R² | R³ | R⁴ | X¹ | X² | X³ | X⁴ | X⁵ | Phys. data (m.p. [°C.]) |
|---|---|---|---|---|---|---|---|---|---|---|
| I-131 | 2,6-dimethyltetrahydropyran-4-yl | | Cl | (CH₃)₂CHCH₂—C(CH₃)=N—OCH₃ | F | F | H | F | H | 82-90 |
| I-132 | 2,6-dimethyltetrahydropyran-4-yl | | Cl | cyclopentyl=N—OCH₃ | F | F | H | F | H | oil |
| I-133 | 2,6-dimethyltetrahydropyran-4-yl | | Cl | cyclohexyl=N—OCH₃ | F | F | H | F | H | oil |
| I-134 | 2,6-dimethyltetrahydropyran-4-yl | | Cl | (CH₃)₃C—C(CH₃)=N—OCH₃ | F | F | H | F | H | oil |
| I-135 | 2,6-dimethyltetrahydropyran-4-yl | | Cl | (CH₃)₂CHCH₂—C(CH₃)=N—OCH₃ | F | F | H | F | H | 96 |
| I-136 | 2,6-dimethyltetrahydropyran-4-yl | | Cl | (CH₃)₃C—C(CH₃)=N—OCH₃ | F | F | H | F | H | 72 |
| I-137 | 2,6-dimethyltetrahydropyran-4-yl | | Cl | —ON=CH—C₆H₅ | F | F | H | F | H | 125 |
| I-138 | 2,6-dimethyltetrahydropyran-4-yl | | Cl | —ON=C(CH₃)—C₆H₅ | F | F | H | F | H | 119 |
| I-139 | 2,6-dimethyltetrahydropyran-4-yl | | Cl | —O—N=CH(2,6-Cl₂—C₆H₃) | F | F | H | F | H | 154 |
| I-140 | —(CH₂)₂CH(CH₃)(CH₂)₂— | | Cl | —O—N=C(CH₃)₂ | CH₃ | CH₃ | H | H | H | oil |
| I-141 | —(CH₂)₂CH(CH₃)(CH₂)₂— | | Cl | —O—N=C(CH₃)₂ | F | F | H | F | H | 98-102 |
| I-142 | —(CH₂)₂CH(CH₃)(CH₂)₂— | | CH₃ | —O—N=C(CH₃)₂ | F | F | H | F | H | oil |

TABLE I-continued

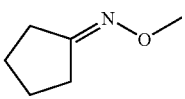

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-143 | —(CH₂)₂CH(CH₃)(CH₂)₂— | | Cl | cyclopentanone O-methyl oxime | F | F | H | F | H | oil |
| I-144 | —(CH₂)₂CH(CH₃)(CH₂)₂— | | Cl | cyclohexanone O-methyl oxime | F | F | H | F | H | oil |
| I-145 | —(CH₂)₂CH(CH₃)(CH₂)₂— | | Cl | 4-methylpentan-2-one O-methyl oxime | F | F | H | F | H | oil |
| I-146 | —(CH₂)₂CH(CH₃)(CH₂)₂— | | Cl | —ON═C(CH₃)—OCH₂CH₃ | F | F | H | F | H | 70 |
| I-147 | —(CH₂)₂CH(CH₃)(CH₂)₂— | | Cl | —ON═CH—C₆H₅ | F | F | H | F | H | oil |
| I-148 | —(CH₂)₂CH(CH₃)(CH₂)₂— | | Cl | —ON═C(CH₃)—C₆H₅ | F | F | H | F | H | 96 |
| I-149 | —(CH₂)₂CH(CH₃)(CH₂)₂— | | Cl | —O—N═CH(2,6-Cl₂—C₆H₃) | F | H | H | F | H | 128 |
| I-150 | —(CH₂)₂CH(CH₃)(CH₂)₂— | | OCH₃ | —ON═C(CH₃)—OCH₂CH₃ | F | F | H | F | H | oil |
| I-151 | —(CH₂)₂CH(CH₃)(CH₂)₂— | | OCH₃ | cyclopentanone O-methyl oxime | CH₃ | H | H | F | H | 105 |
| I-152 | —(CH₂)₂CH(CH₃)(CH₂)₂— | | OCH₃ | cyclohexanone O-methyl oxime | F | F | H | F | H | oil |
| I-153 | —(CH₂)₂CH(CH₃)(CH₂)₂— | | OCH₃ | cyclopentanone O-methyl oxime | F | F | H | F | H | oil |
| I-154 | —(CH₂)₂CH(CH₃)(CH₂)₂— | | OCH₃ | —ON═CH—C₆H₅ | F | F | H | F | H | oil |
| I-155 | —(CH₂)₂CH(CH₃)(CH₂)₂— | | OCH₃ | —O—N═CH(2,6-Cl₂—C₆H₃) | F | H | H | F | H | oil |
| I-156 | —(CH₂)₂CH(CH₃)(CH₂)₂— | | Cl | —OH | F | F | H | F | H | 239-242 |
| I-157 | —(CH₂)₂CH(CH₃)(CH₂)₂— | | Cl | —CH₃ | F | F | H | F | H | oil |
| I-158 | —(CH₂)₂CH(CH₃)(CH₂)₂— | | Cl | —CH₂CH₃ | F | F | H | F | H | oil |
| I-159 | —(CH₂)₂CH(CH₃)(CH₂)₂— | | OCH₃ | —CN | F | F | H | F | H | 106-124 |

TABLE I-continued

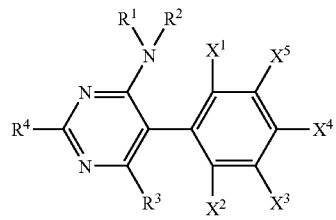

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-160 | —(CH$_2$)$_2$CH(CH$_3$)(CH$_2$)$_2$— | | Cl | —CN | F | F | H | F | H | oil |
| I-161 | —(CH$_2$)$_2$CH(CH$_3$)(CH$_2$)$_2$— | | Cl | pyridin-2-yl-O—C≡C— | F | F | H | F | H | oil |
| I-162 | —(CH$_2$)$_2$CH(CH$_3$)(CH$_2$)$_2$— | | Cl | —C(CH$_3$)=N—OCH$_3$ | F | F | H | F | H | 117 |
| I-163 | —(CH$_2$)$_2$CH(CH$_3$)(CH$_2$)$_2$— | | Cl | —C(CH$_3$)=N—OCH$_2$CH$_3$ | F | F | H | F | H | oil |
| I-164 | —(CH$_2$)$_2$CH(CH$_3$)(CH$_2$)$_2$— | | Cl | —C(CH$_3$)=N—O(CH$_2$)$_2$CH$_3$ | F | F | H | F | H | oil |
| I-165 | —(CH$_2$)$_2$CH(CH$_3$)(CH$_2$)$_2$— | | Cl | —C(CH$_3$)=N—OCH(CH$_3$)$_2$ | F | F | H | F | H | oil |
| I-166 | —(CH$_2$)$_2$CH(CH$_3$)(CH$_2$)$_2$— | | Cl | —C(CH$_3$)=N—O(CH$_2$)$_3$CH$_3$ | F | F | H | F | H | oil |
| I-167 | —(CH$_2$)$_2$CH(CH$_3$)(CH$_2$)$_2$— | | Cl | —C(CH$_3$)=N—OC(CH$_2$)$_3$ | F | F | H | F | H | oil |
| I-168 | —(CH$_2$)$_2$CH(CH$_3$)(CH$_2$)$_2$— | | Cl | —C(CH$_3$)=N—OCH$_2$CH=CHCl | F | F | H | F | H | oil |
| I-169 | —(CH$_2$)$_2$CH(CH$_3$)(CH$_2$)$_2$— | | Cl | —C(CH$_3$)=N—OCH$_2$CH=CH$_2$ | F | F | H | F | H | oil |
| I-170 | —(CH$_2$)$_2$CH(CH$_3$)(CH$_2$)$_2$— | | Cl | —C(CH$_3$)=N—OCH$_2$CCl=CH$_2$ | F | F | H | F | H | oil |
| I-171 | —(CH$_2$)$_2$CH(CH$_3$)(CH$_2$)$_2$— | | Cl | —C(CH$_3$)=N—O(CH$_2$)$_2$OCH$_3$ | F | F | H | F | H | oil |
| I-172 | —(CH$_2$)$_2$CH(CH$_3$)(CH$_2$)$_2$— | | Cl | PhO—CH(CH$_3$)CH$_2$—O—N=C(CH$_3$)— | F | F | H | F | H | oil |
| I-173 | —(CH$_2$)$_2$CH(CH$_3$)(CH$_2$)$_2$— | | Cl | (CH$_3$)$_3$C—O—C(=O)CH$_2$—O—N=C(CH$_3$)— | F | F | H | F | H | oil |
| I-174 | —(CH$_2$)$_2$CH(CH$_3$)(CH$_2$)$_2$— | | Cl | —C(CH$_3$)=N—NH—C(CH$_3$)$_2$ | F | F | H | F | H | oil |
| I-175 | —(CH$_2$)$_2$CH(CH$_3$)(CH$_2$)$_2$— | | Cl | piperidin-1-yl—N=C(CH$_3$)— | F | F | H | F | H | oil |
| I-176 | —(CH$_2$)$_2$CH(CH$_3$)(CH$_2$)$_2$— | | Cl | pyrrolidin-1-yl—N=C(CH$_3$)— | F | F | H | F | H | oil |

TABLE I-continued

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-177 | —(CH₂)₂CH(CH₃)(CH₂)₂— | | Cl | (S)-2-(methoxymethyl)pyrrolidin-1-yl N=C(CH₃)— | F | F | H | F | H | oil |
| I-178 | —(CH₂)₂CH(CH₃)(CH₂)₂— | | Cl | (R)-2-(methoxymethyl)pyrrolidin-1-yl N=C(CH₃)— | F | F | H | F | H | oil |
| I-179 | —(CH₂)₂CH(CH₃)(CH₂)₂— | | Cl | 2,5-dimethylpyrrolidin-1-yl N=C(CH₃)— | F | F | H | F | H | oil |
| I-180 | —(CH₂)₂CH(CH₃)(CH₂)₂— | | Cl | C₆H₅NH—N=C(CH₃)— | F | F | H | F | H | oil |
| I-181 | —(CH₂)₂CH(CH₃)(CH₂)₂— | | Cl | —C(CH₃)=N—N(CH₃)—C₆H₅ | F | F | H | F | H | oil |
| I-182 | —(CH₂)₂CH(CH₃)(CH₂)₂— | | Cl | 1,1-dioxothiomorpholin-4-yl N=C(CH₃)— | F | F | H | F | H | oil |
| I-183 | —(CH₂)₂CH(CH₃)(CH₂)₂— | | Cl | morpholin-4-yl N=C(CH₃)— | F | F | H | F | H | oil |
| I-184 | —(CH₂)₂CH(CH₃)(CH₂)₂— | | Cl | 4-methylpiperazin-1-yl N=C(CH₃)— | F | F | H | F | H | oil |
| I-185 | —(CH₂)₂CH(CH₃)(CH₂)₂— | | Cl | —C(NH₂)=N—OH | F | F | H | F | H | oil |
| I-186 | —(CH₂)₂CH(CH₃)(CH₂)₂— | | Cl | —C(NH₂)=N—OCH₃ | F | F | H | F | H | oil |
| I-187 | —(CH₂)₂CH(CH₃)(CH₂)₂— | | Cl | CH₃O—N=C(C₂H₅)— | F | F | H | F | H | oil |

TABLE I-continued

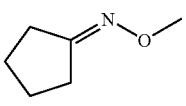

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-188 | —(CH₂)₂CH(CH₃)(CH₂)₂— | | Cl | —CN | CH₃ | CH₃ | H | H | H | oil |
| I-189 | —(CH₂)₂CH(CH₃)(CH₂)₂— | | Cl | —O—N=C(CH₃)₂ | F | F | H | OCH₃ | H | oil |
| I-190 | —(CH₂)₂CH(CH₃)(CH₂)₂— | | Cl | cyclopentanone O-methyloxime | F | F | H | OCH₃ | H | oil |
| I-191 | —(CH₂)₂CH(CH₃)(CH₂)₂— | | Cl | cyclohexanone O-methyloxime | F | F | H | OCH₃ | H | oil |
| I-192 | —(CH₂)₂CH(CH₃)(CH₂)₂— | | Cl | —CN | F | F | H | OCH₃ | H | oil |
| I-193 | —(CH₂)₂CH(CH₃)(CH₂)₂— | | Cl | —CH₃ | F | F | H | OCH₃ | H | oil |
| I-194 | —(CH₂)₂CH(CH₃)(CH₂)₂— | | Cl | —O—N=C(CH₃)₂ | Cl | F | H | H | H | 109 |
| I-195 | —(CH₂)₂CH(CH₃)(CH₂)₂— | | Cl | cyclopentanone O-methyloxime | Cl | F | H | H | H | oil |
| I-196 | —(CH₂)₂CH(CH₃)(CH₂)₂— | | Cl | cyclohexanone O-methyloxime | Cl | F | H | H | H | oil |
| I-197 | —(CH₂)₂CH(CH₃)(CH₂)₂— | | Cl | —O—N=CH(2,6-Cl₂—C₆H₃) | Cl | F | H | H | H | 126 |
| I-198 | —(CH₂)₂CH(CH₃)(CH₂)₂— | | Cl | —OH | Cl | F | H | H | H | 164-169 |
| I-199 | —(CH₂)₂CH(CH₃)(CH₂)₂— | | Cl | —O—CH₂CH₃ | Cl | F | H | H | H | oil |
| I-200 | —(CH₂)₂CH(CH₃)(CH₂)₂— | | Cl | —O—CH₂CH(CH₃)CH₂CH=CH₂ | Cl | F | H | H | H | oil |
| I-201 | —(CH₂)₂CH(CH₃)(CH₂)₂— | | Cl | —NHCH₂CH₂N(CH₃)₂ | Cl | F | H | H | H | 107-109 |
| I-202 | —(CH₂)₂CH(CH₃)(CH₂)₂— | | Cl | —N(CH₂CH₂)₂ | Cl | F | H | H | H | oil |
| I-203 | —(CH₂)₂CH(CH₃)(CH₂)₂— | | Cl | —CH₂CH₃ | Cl | F | H | H | H | oil |
| I-204 | —(CH₂)₂CH(CH₃)(CH₂)₂— | | Cl | —CH(CH₃)₂ | Cl | F | H | H | H | oil |
| I-205 | —(CH₂)₂CH(CH₃)(CH₂)₂— | | Cl | —CH₂CH=CH₂ | Cl | F | H | H | H | oil |
| I-206 | —(CH₂)₂CH(CH₃)(CH₂)₂— | | Cl | —CN | Cl | F | H | H | H | oil |

TABLE I-continued

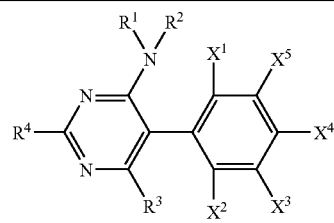

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-207 | —(CH$_2$)$_2$CH(CH$_3$)(CH$_2$)$_2$— | | Cl | —S—CH$_3$ | F | H | H | H | H | oil |
| I-208 | —(CH$_2$)$_2$CH(CH$_3$)(CH$_2$)$_2$— | | Cl | —O—N=C(CH$_3$)$_2$ | F | H | H | CH$_3$ | H | oil |
| I-209 | —(CH$_2$)$_2$CH(CH$_3$)(CH$_2$)$_2$— | | Cl | 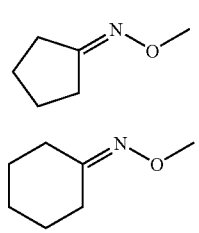 | F | H | H | CH$_3$ | H | 136 |
| I-210 | —(CH$_2$)$_2$CH(CH$_3$)(CH$_2$)$_2$— | | Cl | 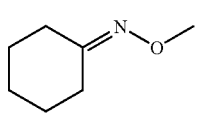 | F | H | H | CH$_3$ | H | oil |
| I-211 | —(CH$_2$)$_2$CH(CH$_3$)(CH$_2$)$_2$— | | Cl | —CN | F | H | H | CH$_3$ | H | 95-97 |
| I-212 | —(CH$_2$)$_2$CH(CH$_3$)(CH$_2$)$_2$— | | OCH$_3$ | —O—N=C(CH$_3$)$_2$ | F | H | H | CH$_3$ | H | oil |
| I-213 | —(CH$_2$)$_2$CH(CH$_3$)(CH$_2$)$_2$— | | Cl | —O—N=C(CH$_3$)$_2$ | F | H | H | CH$_3$ | H | oil |
| I-214 | —(CH$_2$)$_2$CH(CH$_3$)(CH$_2$)$_2$— | | Cl | | F | H | H | CH$_3$ | H | oil |
| I-215 | —(CH$_2$)$_2$CH(CH$_3$)(CH$_2$)$_2$— | | Cl | —O—N=CH(2,6-Cl$_2$—C$_6$H$_3$) | F | H | H | CH$_3$ | H | 148 |
| I-216 | —CH$_2$SCH$_2$CH$_2$— | | Cl | —S—CH$_3$ | F | H | H | H | H | oil |
| I-217 | CH$_2$CH$_3$ | CH$_2$CH$_3$ | Cl | —S—CH$_3$ | F | H | H | H | H | oil |
| I-218 | CH(CH$_3$)$_2$ | CH$_3$ | Cl | —CH$_3$ | H | H | F | H | H | 75-77 |
| I-219 | CH(CH$_3$)$_2$ | H | Cl | —O—N=C(CH$_3$)CF$_3$ | F | F | H | F | H | 205-207 |
| I-220 | CH(CH$_3$)$_2$ | H | Cl | —NH—N=C(CH$_3$)—C$_6$H$_5$ | F | F | H | F | H | 185-187 |
| I-221 | CH(CH$_3$)$_2$ | H | Cl | —NH—N=C(CH$_3$)—C$_6$H$_5$ | F | F | H | F | H | 84-87 |
| I-222 | CH(CH$_3$)$_2$ | H | Cl | —NH—N=CH—C$_6$H$_5$ | F | F | H | F | H | 138-140 |
| I-223 | CH(CH$_3$)$_2$ | H | Cl | —O—CH$_2$CH$_3$ | F | F | H | F | H | oil |
| I-224 | CH(CH$_3$)$_2$ | H | Cl | —O—CH$_3$ | F | F | H | F | H | 137-139 |
| I-225 | CH(CH$_3$)$_2$ | H | Cl | —O—CH$_2$CH$_2$CH$_3$ | F | F | H | F | H | oil |

TABLE I-continued

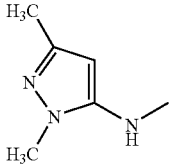

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-226 | CH(CH₃)₂ | H | Cl | —S—CH₂CH₃ | F | F | H | F | H | oil |
| I-227 | CH(CH₃)₂ | H | Cl | —S—CH(CH₃)CH₃CH₂ | F | F | H | F | H | oil |
| I-228 | CH(CH₃)₂ | H | Cl | —S—CH₃ | F | F | H | F | H | 112-116 |
| I-229 | CH(CH₃)₂ | H | Cl | —S—CH(CH₃)₂ | F | F | H | F | H | oil |
| I-230 | CH(CH₃)₂ | H | Cl | —S—CH₂CH₂CH₃ | F | F | H | F | H | 95-98 |
| I-231 | CH(CH₃)₂ | H | Cl | —N(CH₃)₂ | Cl | F | H | H | H | 91-94 |
| I-232 | CH(CH₃)₂ | H | Cl | —NHOCH₃ | Cl | F | H | H | H | 151-153 |
| I-233 | CH(CH₃)₂ | H | Cl | —NH—C₆H₅ | Cl | F | H | H | H | oil |
| I-234 | CH(CH₃)₂ | H | Cl | 3,5-dimethyl-1-methyl-pyrazol-5-yl-NH- (H₃C, N-N, H₃C, NH) | Cl | F | H | H | H | oil |
| I-235 | CH(CH₃)₂ | H | Cl | —O—CH₃ | Cl | F | H | H | H | 147-149 |
| I-236 | CH(CH₃)₂ | H | Cl | —O—CH₂CH₃ | Cl | F | H | H | H | 165-168 |
| I-237 | CH(CH₃)₂ | H | Cl | —O—CH₂CH₂CH₃ | Cl | F | H | H | H | 110-112 |
| I-238 | CH(CH₃)₂ | H | Cl | —O—CH(CH₃)₂ | Cl | F | H | H | H | 125-127 |
| I-239 | CH(CH₃)₂ | H | Cl | —O—C(CH₃)₃ | Cl | F | H | H | H | 118-121 |
| I-240 | CH(CH₃)₂ | H | Cl | —O—CH₂CH₂CH₂CH₃ | Cl | F | H | H | H | 98-100 |
| I-241 | CH(CH₃)₂ | H | Cl | —O—CH(CH₃)CH₂CH₃ | Cl | F | H | H | H | 108-111 |
| I-242 | CH(CH₃)₂ | H | Cl | —S—CH₃ | Cl | F | H | H | H | 106-110 |
| I-243 | CH(CH₃)₂ | H | Cl | —S—CH₂CH₂CH₃ | Cl | F | H | H | H | oil |
| I-244 | CH(CH₃)₂ | H | Cl | —S—CH(CH₃)₂ | Cl | F | H | H | H | 111-113 |
| I-245 | CH(CH₃)₂ | H | Cl | —S—C(CH₃)₃ | Cl | F | H | H | H | 94-96 |
| I-246 | CH(CH₃)₂ | H | Cl | —S—CH₂CH₂CH₂CH₃ | Cl | F | H | H | H | oil |

TABLE I-continued

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-247 | CH(CH₃)₂ | H | Cl | —S—CH(CH₃)CH₂CH₃ | Cl | F | H | H | H | 114-117 |
| I-248 | CH(CH₃)₂ | H | Cl | —S—CH₂CH₃ | Cl | F | H | H | H | 104-108 |
| I-249 | CH(CH₃)₂ | H | Cl | —CN | Cl | F | H | H | H | 186-188 |
| I-250 | CH(CH₃)₂ | H | Cl | —S—CH₃ | F | H | H | H | H | oil |
| I-251 | CH₂CH=CH₂ | H | Cl | —S—CH₃ | F | H | H | H | H | 124-126 |
| I-252 | CH₂—C₆H₅ | H | Cl | —S—CH₃ | F | H | H | H | H | 135-137 |
| I-253 | (S)—CH(CF₃)CH₃ | H | Cl | —O—N=CHCH₃ | F | F | H | F | H | 139-141 |
| I-254 | (S)—CH(CF₃)CH₃ | H | Cl | —O—N=C(CH₃)₂ | F | F | H | F | H | 157-159 |
| I-255 | (S)—CH(CF₃)CH₃ | H | Cl | cyclopentanone O-methyl oxime | F | F | H | F | H | 88-92 |
| I-256 | (S)—CH(CF₃)CH₃ | H | Cl | cyclohexanone O-methyl oxime | F | F | H | F | H | 176-179 |
| I-257 | (S)—CH(CF₃)CH₃ | H | Cl | —ON=C(CH₃)—OCH₂CH₃ | F | F | H | F | H | 110-112 |
| I-258 | (S)—CH(CF₃)CH₃ | H | Cl | (CH₃)₃C—C(CH₃)=N—OCH₃ | F | F | H | F | H | 350 |
| I-259 | (S)—CH(CF₃)CH₃ | H | Cl | (CH₃)₂CHCH₂—C(CH₃)=N—OCH₃ | F | F | H | F | H | 68-70 |
| I-260 | (S)—CH(CF₃)CH₃ | H | Cl | —ON=CH—C₆H₅ | F | F | H | F | H | 145-146 |
| I-261 | (S)—CH(CF₃)CH₃ | H | Cl | —ON=C(CH₃)C₆H₅ | F | F | H | F | H | 151-155 |
| I-262 | (S)—CH(CF₃)CH₃ | H | Cl | —O—N=CH(2,6-Cl₂—C₆H₃) | F | F | H | F | H | 87-90 |

TABLE I-continued

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-263 | (S)—CH(CF₃)CH₃ | H | Cl | bis(pyridin-2-yl)methanone O-methyl oxime | F | F | H | F | H | 84-86 |
| I-264 | (S)—CH(CF₃)CH₃ | H | Cl | 1,1,1-trifluoro-N',N'-dimethylpropan-2-yl hydrazine | F | F | H | F | H | oil |
| I-265 | (S)—CH(CF₃)CH₃ | H | Cl | —N(CH₃)—N=C(CH₃)—C₆H₅ | F | F | H | F | H | oil |
| I-266 | (S)—CH(CF₃)CH₃ | H | Cl | —N(CH₃)—N=CH—C₆H₅ | F | F | H | F | H | 152-155 |
| I-267 | (S)—CH(CF₃)CH₃ | H | Cl | —N(CH₃)—N=C(CH₃)₂ | F | F | H | F | H | 205-208 |
| I-268 | (S)—CH(CF₃)CH₃ | H | Cl | —NH—C(=NH)CH₃ | F | F | H | F | H | oil |
| I-269 | (S)—CH(CF₃)CH₃ | H | Cl | —NH—NH—C₆H₅ | F | F | H | F | H | oil |
| I-270 | (S)—CH(CF₃)CH₃ | H | Cl | 4-chloro-1H-pyrazol-1-yl methylamine | F | F | H | F | H | 132-134 |
| I-271 | (S)—CH(CF₃)CH₃ | H | Cl | —N(CH₃)—NH₂ | F | F | H | F | H | 126-128 |
| I-272 | (S)—CH(CF₃)CH₃ | H | Cl | —NH—NH—CH₂CF₃ | F | F | H | F | H | oil |
| I-273 | (S)—CH(CF₃)CH₃ | H | Cl | —N₃ | F | F | H | F | H | 152-154 |
| I-274 | (S)—CH(CF₃)CH₃ | H | Cl | —OH | F | F | H | F | H | 137-146 |
| I-275 | (S)—CH(CF₃)CH₃ | H | Cl | —O—CH₃ | F | F | H | F | H | 121-129 |
| I-276 | (S)—CH(CF₃)CH₃ | H | Cl | —O—CH₂CH₃ | F | F | H | F | H | 147-149 |
| I-277 | (S)—CH(CF₃)CH₃ | H | Cl | —O—CH(CH₃)₂ | F | F | H | F | H | 159-161 |
| I-278 | (S)—CH(CF₃)CH₃ | H | Cl | —O—CH₂CH₂CH₂CH₃ | F | F | H | F | H | 116-117 |
| I-279 | (S)—CH(CF₃)CH₃ | H | Cl | —O—CH(CH₃)CH₂CH₃ | F | F | H | F | H | 129-131 |
| I-280 | (S)—CH(CF₃)CH₃ | H | Cl | —S—CH₂CH₃ | F | F | H | F | H | oil |

TABLE I-continued

[Structure: pyrimidine with NR¹R² at 4-position, R³ at 6-position, R⁴ at 2-position, and a phenyl group at 5-position bearing X¹, X², X³, X⁴, X⁵ substituents]

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-281 | (S)—CH(CF₃)CH₃ | H | Cl | —S—CH₂CH₂CH₃ | F | F | H | F | H | 68-69 |
| I-282 | (S)—CH(CF₃)CH₃ | H | Cl | —S—CH(CH₃)₂ | F | F | H | F | H | 73-76 |
| I-283 | (S)—CH(CF₃)CH₃ | H | Cl | —S—C(CH₃)₃ | F | F | H | F | H | oil |
| I-284 | (S)—CH(CF₃)CH₃ | H | Cl | —S—CH₂CH₂CH₂CH₃ | F | F | H | F | H | oil |
| I-285 | (S)—CH(CF₃)CH₃ | H | Cl | —S—CH(CH₃)CH₂CH₃ | F | F | H | F | H | 64-65 |
| I-286 | (S)—CH(CF₃)CH₃ | H | Cl | —CH₃ | F | F | H | F | H | 83-85 |
| I-287 | (S)—CH(CF₃)CH₃ | H | Cl | —CN | F | F | H | F | H | 134-136 |
| I-288 | (S)—CH(CF₃)CH₃ | H | Cl | —CH₃ | Cl | F | H | H | H | 87-90 |
| I-289 | (R/S)—CH(CF₃)CH₃ | H | Cl | —O—N=C(CH₃)₂ | F | F | H | F | H | 82 |
| I-290 | (R/S)—CH(CF₃)CH₃ | H | Cl | cyclopentanone O-methyl oxime | F | F | H | F | H | 130 |
| I-291 | (R/S)—CH(CF₃)CH₃ | H | Cl | cyclohexanone O-methyl oxime | F | F | H | F | H | 69 |
| I-292 | (R/S)—CH(CF₃)CH₃ | H | Cl | —ON=C(CH₃)—OCH₂CH₃ | F | F | H | F | H | 120 |
| I-293 | (R/S)—CH(CF₃)CH₃ | H | Cl | (CH₃)₂CHCH₂—C(=N—OCH₃)—CH₃ | F | F | H | F | H | 87 |
| I-294 | (R/S)—CH(CF₃)CH₃ | H | Cl | (CH₃)₃C—C(=N—OCH₃)—CH₃ | F | F | H | F | H | 97 |
| I-295 | (R/S)—CH(CF₃)CH₃ | H | Cl | —ON=CH—C₆H₅ | F | F | H | F | H | 140 |
| I-296 | (R/S)—CH(CF₃)CH₃ | H | Cl | —ON=C(CH₃)—C₆H₅ | F | F | H | F | H | 175 |
| I-297 | (R/S)—CH(CF₃)CH₃ | H | Cl | —ON=CH—(2,6-Cl₂—C₆H₃) | F | F | H | F | H | 157 |

TABLE I-continued

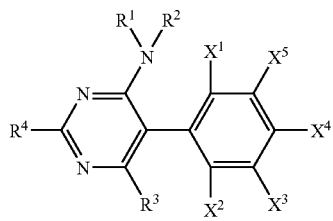

| No. | R¹ | R² | R³ | R⁴ | X¹ | X² | X³ | X⁴ | X⁵ | Phys. data (m.p. [° C.]) |
|---|---|---|---|---|---|---|---|---|---|---|
| I-298 | (R/S)—CH(CF₃)CH₃ | H | Cl | Cl-C₆H₄-NH-C(=NH)-NH-CH₃ | F | F | H | F | H | oil |
| I-299 | (R/S)—CH(CF₃)CH₃ | H | Cl | —N(CH₃)₂ | F | F | H | F | H | 108-112 |

The R⁴ groups are attached to the pyrimidine skeleton via the free valencies.
Owing to their C=C, C=N and N=N double bonds, the groups R⁴ can be present as E/Z isomer mixtures.

EXAMPLES OF THE ACTIVITY AGAINST HARMFUL FUNGI

The fungicidal activity of the compounds of the formula I was demonstrated by the following experiments:

The active compounds were formulated, separately or together, as a 10% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Wettol® EM (nonionic emulsifier based on ethoxylated castor oil) and diluted with water to the desired concentration.

Use Example 1

Activity against Septoria Leaf Blotch of Wheat (*Septoria tritici*)

Leaves of potted wheat seedlings of the cultiva "Riband" were sprayed to runoff point with an aqueous preparation of active compound which had been prepared from a stock solution comprising 10% of active compound, 85% of cyclohexanone and 5% of emulsifier. 24 hours after the spray coating had dried on, the seedlings were inoculated with an aqueous spore suspension of *Septoria tritici*. The suspension contained 2.0×10⁶ spores/ml. The test plants were then placed in a greenhouse at temperatures between 18 and 22° C. and a relative atmospheric humidity close to 100%. After 2 weeks, the extent of the development of the disease was determined visually in % infection of the total leaf area.

In this test, the plants which had been treated with 250 ppm of the active compounds Nos. 1, 12 to 15, 18, 19, 21, 24 to 26, 30, 32, 33, 54, 55, 60, 61 to 65, 86, 160, 223, 224, 226, 228, 235 to 239, 248, 254, 264, 265, 269, 270, 271, 272 and 275 to 278 of Table I showed an infection of at most 7%, whereas the untreated plants were 90% infected.

Use Example 2

Activity against Net Blotch of Barley (*Pyrenophora teres*)

Leaves of potted barley seedlings of the cultivar "Igri" were sprayed to runoff point with an aqueous preparation of active compound which had been prepared from a stock solution comprising 10% of active compound, 85% of cyclohexanone and 5% of emulsifier and, 24 hours after the spray coating had dried on, inoculated with an aqueous spore suspension of *Pyrenophora* [syn. *Drechslera*] *teres*, the net blotch pathogen. The test plants were then placed in a greenhouse at temperatures between 20 and 24° C. and at 95-100% relative atmospheric humidity. After 6 days, the extent of the development of the disease was determined visually in % infection of the total leaf area.

In this test, the plants which had been treated with 250 ppm of the active compounds Nos. 1, 55, 60, 64, 73, 88, 130, 134, 160, 163, 165, 168, 171, 185, 186, 254, 255, 265, 267, 271, 274, 276, 277, 278 and 287 of Table I showed an infection of not more than 15%, whereas the untreated plants were 100% infected.

Use Example 3

Protective Activity against Mildew of Cucumber Caused by *Sphaerotheca fuliginea*

Leaves of potted cucumber seedlings of the cultivar "Chinese Snake" were, at the cotyledon stage, sprayed to runoff point with an aqueous preparation of active compound which had been prepared from a stock solution comprising 10% of active compound, 85% of cyclohexanone and 5% of emulsifier 20 hours after the spray coating had dried on, the plants were inoculated with an aqueous spore suspension of mildew of cucumber (*Sphaerotheca fuliginea*). The plants were then cultivated in a greenhouse at 20-24° C. and 60-80% relative atmospheric humidity for 7 days. The extent of the mildew development was then determined visually in % infection of the cotyledon area.

In this test, the plants which had been treated with 250 ppm of the active compounds Nos. 86, 88, 100, 121, 130, 141, 160, 163, 168, 171, 185, 186, 189, 206, 220, 249, 253 to 261, 265, 266, 271, 273, 275, 276, 287 and 299 of Table I showed an infection of not more than 10%, whereas the untreated plants were 85% infected.

We claim:

1. A 5-phenylpyrimidine of the formula I

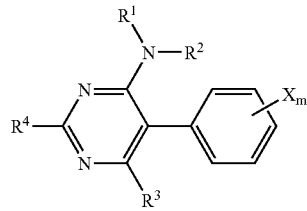

where the substituents and the index are as defined below:
- $R^1$ is $C_1$—$C_6$-alkyl, $C_1$—$C_6$-haloalkyl, $C_3$—$C_6$cycloalkyl, $C_3$—$C_6$-halo-cycloalkyl, $C_2$—$C_6$-alkenyl, $C_2$—$C_6$-haloalkenyl, $C_2$—$C_6$-alkynyl or $C_2$—$C_6$-haloalkynyl,
- $R^2$ is hydrogen or a group as defined for $R^1$, or
- $R^1$ and $R^2$ together with the nitrogen atom to which they are attached may also form a saturated or unsaturated five- or six-membered ring which may be interrupted by an ether- (—O—), thio- (—S—), sulfoxyl- (—S[=O]—) or sulfenyl- (—SO$_2$—) group and/or may be substituted by one to four groups $R^a$ and/or $R^b$;
- $R^a$, $R^b$ independently of one another are hydrogen, $C_1$—$C_6$-alkyl, $C_2$—$C_8$-alkenyl, $C_2$—$C_8$-alkynyl, $C_1$—$C_6$-haloalkyl, $C_1$—$C_6$-alkoxy, $C_1$—$C_6$-haloalkoxy, $C_3$—$C_{10}$-cycloalkyl, phenyl or a five- to ten-membered saturated, partially unsaturated or aromatic heterocycle containing one to four heteroatoms from the group consisting of O, N and S, where the cyclic radicals may be partially or fully substituted by the following groups $R^x$; or
- $R^a$ and $R^b$ together, via an alkylene or alkenylene chain with the bridging atom, may also form a saturated or unsaturated 5- or 6- membered ring;
- $R^x$ independently of one another are cyano, nitro, amino, aminocarbonyl, aminothiocarbonyl, halogen, hydroxyl, $C_1$—$C_6$-alkyl, $C_1$—$C_6$-haloalkyl, $C_1$—$C_6$-alkylcarbonyl, $C_1$—$C_6$-alkylsulfonyl, $C_1$—$C_6$-alkylsulfoxyl, $C_3$—$C_6$-cycloalkyl, $C_1$—$C_6$-alkoxy, $C_1$—$C_6$-haloalkoxy, $C_1$—$C_6$-alkyloxycarbonyl, $C_1$—$C_6$-alkylthio, $C_1$—$C_6$-alkylamino, di-$C_1$—$C_6$-alkylamino, $C_1$—$C_6$-alkylaminocarbonyl, di-$C_1$—$C_6$-alkylaminocarbonyl, $C_1$—$C_6$-alkylaminothiocarbonyl, di-$C_1$—$C_6$-alkylaminothiocarbonyl, $C_2$—$C_6$-alkenyl, $C_2$—$C_6$-alkenyloxy, phenyl, phenoxy, benzyl, benzyloxy, 5- or 6-membered heterocyclyl, 5- or 6-membered hetaryl, 5 -or 6-membered hetaryloxy, $C(=NOR^\alpha)$—$OR^\beta$ or $OC(R^\alpha)_2$—$C(R^\beta)$=$NOR^\beta$- where the cyclic groups for their part are unsubstituted or substituted by one to three radicals $R^y$;
- $R^y$ is cyano, nitro, halogen, hydroxyl, amino, aminocarbonyl, aminothiocarbonyl, $C_1$—$C_6$-alkyl, $C_1$—$C_6$-haloalkyl, $C_1$—$C_6$-alkylsulfonyl, $C_1$—$C_6$-alkylsulfoxyl, $C_3$—$C_6$-cycloalkyl, $C_1$—$C_6$-alkoxy, $C_1$—$C_6$-haloalkoxy, $C_1$—$C_6$-alkoxycarbonyl, $C_1$—$C_6$-alkylthio, $C_1$—$C_6$-alkylamino, di-$C_1$—$C_6$-alkylamino, $C_1$—$C_6$-alkylaminocarbonyl,di-$C_1$—$C_6$-alkylaminocarbonyl, $C_1$—$C_6$-alkylaminothiocarbonyl, di-$C_1$—$C_6$-alkylaminothiocarbonyl, $C_2$—$C_6$-alkenyl, $C_2$—$C_6$-alkenyloxy, $C_2$—$C_6$-cycloalkyl, $C_3$—$C_6$-cycloalkenyl, phenyl, phenoxy, phenylthio, benzyl, benzyloxy, 5- or 6-membered heterocyclyl, 5 - or 6-membered hetaryl, 5- or 6-membered hetaryloxy or $C(=NOR^\alpha)$—$OR^\beta$;
- $R^\alpha$, $R^\beta$ are hydrogen or $C_1$—$C_6$-alkyl;
- $R^3$ is halogen, cyano or $C_1$—$C_6$-alkyl;
- $R^4$ is cyano;
- X is halogen, $C_1$—$C_6$-alkyl, $C_1$—$C_6$-alkoxy or $C_1$—$C_6$-haloalkyl; and
- m is an integer from 1 to 5.

2. A 5-phenylpyrimidine of the formula I

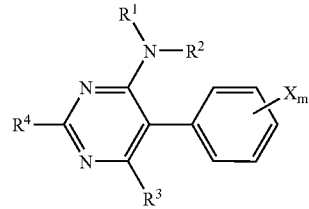

where the substituents and the index are as defined below:
- $R^1$ is $C_1$—$C_6$-alkyl, $C_1$—$C_6$-haloalkyl, $C_3$—$C_6$-cycloalkyl, $C_3$—$C_6$-halocycloalkyl, $C_2$—$C_6$-alkenyl, $C_2$—$C_6$-haloalkenyl, $C_2$—$C_6$-alkynyl or $C_2$—$C_6$-haloalkynyl,
- $R^2$ is hydrogen or a group as defined for $R^1$, or
- $R^1$ and $R^2$ together with the nitrogen atom to which they are attached may also form a saturated or unsaturated five- or six-membered ring which may be interrupted by an oxygen atom and which may carry a $C_1$—$C_6$-alkyl substituent or in which two adjacent carbon ring members may be bridged by a $C_1$—$C_4$-alkylene group;
- $R^3$ is halogen or cyano;
- $R^4$ is cyano;
- X is halogen, $C_1$—$C_6$-alkyl, $C_1$—$C_6$-alkoxy or $C_1$—$C_6$-haloalkyl; and
- m is an integer from 1 to 5.

* * * * *

UNITED STATES PATENT AND TRADEMARK OFFICE
CERTIFICATE OF CORRECTION

PATENT NO.        : 7,449,471 B2
APPLICATION NO.   : 11/677862
DATED             : November 11, 2008
INVENTOR(S)       : Gypser et al.

It is certified that error appears in the above-identified patent and that said Letters Patent is hereby corrected as shown below:

In Claim 1, col. 62, indicated line 14:
"$C_2$-$C_6$-cycloalkyl" should read -- $C_3$-$C_6$-cycloalkyl --

Signed and Sealed this

Tenth Day of March, 2009

JOHN DOLL
*Acting Director of the United States Patent and Trademark Office*